(12) United States Patent
Aizenberg

(10) Patent No.: US 8,917,398 B2
(45) Date of Patent: Dec. 23, 2014

(54) METHOD AND APPARATUS FOR SUPERVISION OF OPTICAL MATERIAL PRODUCTION

(75) Inventor: Gustavo E. Aizenberg, Ness Ziona (IL)

(73) Assignee: G & D Innovative Analysis Ltd., Ness Ziona (IL)

( * ) Notice: Subject to any disclaimer, the term of this patent is extended or adjusted under 35 U.S.C. 154(b) by 646 days.

(21) Appl. No.: 13/219,677

(22) Filed: Aug. 28, 2011

(65) Prior Publication Data
US 2013/0050687 A1 Feb. 28, 2013

(51) Int. Cl.
*G01B 11/06* (2006.01)
*G01N 21/41* (2006.01)

(52) U.S. Cl.
CPC ............ *G01N 21/41* (2013.01); *G01B 11/0633* (2013.01)
USPC .......................................... 356/632; 356/128

(58) Field of Classification Search
CPC .............. G01B 11/06; G01B 11/0625; G01B 11/0683; G01B 7/06; G01B 11/0633; G01N 21/211; G01N 2021/8438; G01N 2021/4126; G01N 21/41
USPC ....................................................... 356/128
See application file for complete search history.

(56) References Cited

U.S. PATENT DOCUMENTS

| | | |
|---|---|---|
| 4,555,767 A | 11/1985 | Case et al. |
| 4,707,611 A | 11/1987 | Southwell |
| 5,387,309 A | 2/1995 | Bobel et al. |
| 5,523,840 A | 6/1996 | Nishizawa et al. |
| 5,587,792 A | 12/1996 | Nishizawa et al. |
| 6,025,596 A | 2/2000 | Shirai et al. |
| 6,515,293 B1 | 2/2003 | Jun et al. |
| 6,654,132 B1 | 11/2003 | Schietinger et al. |
| 7,474,407 B2 | 1/2009 | Gutin |

(Continued)

FOREIGN PATENT DOCUMENTS

| | | |
|---|---|---|
| DE | 4228870 A1 | 3/1994 |
| DE | 102005023734 A1 | 11/2006 |

(Continued)

OTHER PUBLICATIONS

Characterization of electronic materials by optical reflectance spectroscopy and digital signal processing, Mat. Res. Soc. Symp. Proc. vol. 324, 1994.*

(Continued)

*Primary Examiner* — Tarifur Chowdhury
*Assistant Examiner* — Sunghee Y Gray
(74) *Attorney, Agent, or Firm* — Simon Kahn; Chanoch Kahn

(57) ABSTRACT

An apparatus arranged to analyze a multi-layer optical material structure, the apparatus constituted of: a control unit, a light source outputting light; and a light receiver arranged to receive the light from the light source after interaction with the target structure, the control unit arranged to: detect the amplitude of the received light as a function of wavelength; perform a transform of a function of the detected amplitudes to the optical thickness domain; determine, responsive to a planned composition of the target multi-layer structure, optical thickness and amplitude of expected peaks of the performed transform to the optical thickness domain which correspond with interactions with single interface between layers; identify actual peaks of the performed transform to the optical thickness domain which correspond with interfaces between layers; and determine at least one physical characteristic of the target structure responsive to the determined peaks.

14 Claims, 12 Drawing Sheets

(56) References Cited

U.S. PATENT DOCUMENTS

| | | |
|---|---|---|
| 2007/0024850 A1* | 2/2007 | Zaghloul et al. .............. 356/369 |
| 2007/0174014 A1 | 7/2007 | Halm |
| 2010/0007894 A1 | 1/2010 | Suehira |

FOREIGN PATENT DOCUMENTS

| | | |
|---|---|---|
| EP | 0857943 A2 | 8/1998 |
| WO | 98/05066 | 2/1998 |
| WO | 02/04885 A1 | 1/2002 |

OTHER PUBLICATIONS

C J Miner, Non-destructive, whole wafer assessment of optoelectronic epitaxial materials, Semiconductor Science and Technology vol. 7, No. 1A, 1992, Abstract, downloaded on Dec. 28, 2011 from http://iopscience.iop.org/0268-1242/7/1A/002.

* cited by examiner

METHOD AND APPARATUS FOR SUPERVISION OF OPTICAL MATERIAL PRODUCTION

TECHNICAL FIELD

The present disclosure relates generally to the field of control systems for multi-layer optical material structures and in particular to a method and apparatus for providing supervision of thickness and refractive index for optical materials deposited in a multiple layer structure during its fabrication.

BACKGROUND ART

The production of multiple layer optical material structures has become very advanced over the years, and requires careful control during the processing stage to ensure that the layers being deposited, or grown, are of the desired thickness. Additionally, supervision of the actual refractive index, or a function thereof, for each layer, would be a useful metric of the appropriate composition of the layer. As layers are added, one on top of the other, care must be taken to ensure that a clean boundary between layers is defined, and that the boundary does not suffer from diffusion as additional layers are added.

The prior art teaches cleaving a section of the structure, and then analyzing the cleaved section in a scanning electron microscope. Unfortunately this testing suffers from 2 drawbacks, namely it is destructive and slow. To overcome some of these difficulties, Fourier Transform Infrared Spectroscopy was developed, wherein a sample is irradiated with infrared light having a relatively wide wave number range, followed by Fourier transformation of the resultant interference spectrum to produce a space interference waveform. Unfortunately, a direct result of the desired properties and metrics indicated above are not available from the space interference waveform according to the prior art, and instead a numerically intensive method of utilizing an optical characteristic matrix is described, such as in U.S. Pat. No. 5,587,792 issued Dec. 24, 1996 to Nishizawa et al., the entire contents of which is incorporated herein by reference. Such a numerically intensive method causes in-situ evaluation to be cumbersome and relatively slow, in particular as interpretation of the results for a non-trivial number of layers is not direct, but is instead based on curve fitting against theoretical models.

A bilinear transformation of reflectance has been proposed for analysis of the optical thickness. Specifically, a bilinear transformation of reflectance data is followed by a Fourier transform and hence transformed to the optical thickness domain, and the optical thickness peaks thus provide an analysis of the optical thickness of the actual structure. Unfortunately, such a method yields direct results only for small refractive index steps, i.e. wherein the structure to be analyzed does not exhibit refractive index steps greater than about 20%. In the event of large refractive index steps, such a transformation yields numerous peaks in the optical thickness domain, the number of peaks exceeding the number of interfaces. Thus, this method has been deemed unsuitable for analysis of multiple layer optical material structures with large refractive index steps.

SUMMARY OF INVENTION

In view of the discussion provided above and other considerations, the present disclosure provides methods and apparatus to overcome some or all of the disadvantages of prior and present methods of providing analysis of multi-layer optical material structures. Other new and useful advantages of the present methods and apparatus will also be described herein and can be appreciated by those skilled in the art.

In certain embodiments an apparatus arranged to analyze a multi-layer optical material structure is provided, the apparatus comprising: a control unit, a light source arranged to irradiate a target structure; and a light receiver in communication with the control unit and arranged to receive the irradiated light from the light source after interaction with the target structure, the control unit arranged to: detect the amplitude of the received light as a function of wavelength; perform a transform of a function of the detected amplitudes to the optical thickness domain; determine, responsive to a planned composition of the target semiconductor, optical thickness and amplitude of expected peaks of the performed transform to the optical thickness domain which correspond with interfaces between layers; identify, responsive to the expected peaks, actual peaks of the performed transform to the optical thickness domain which correspond with interfaces between layers; and determine at least one physical characteristic of the target structure responsive to the determined actual peaks.

Additional features and advantages of the invention will become apparent from the following drawings and description.

BRIEF DESCRIPTION OF DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DESCRIPTION OF EMBODIMENTS

Figure 1A:
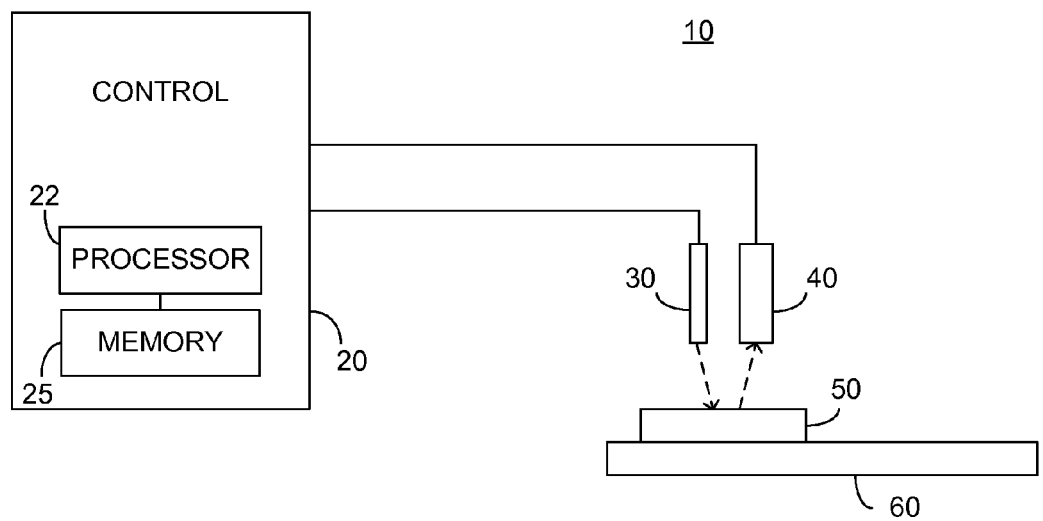
FIG. 1A illustrates a first embodiment of an apparatus arranged to determine at least one physical characteristic of a multi-layer optical material structure responsive to reflected light.

Before explaining at least one embodiment in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting. In particular, the term connected as used herein is not meant to be limited to a direct connection, and allows for intermediary devices or components without limitation.

FIG. 1A illustrates a first embodiment of an apparatus 10 arranged to determine at least one physical characteristic of a multi-layer optical material structure 50 responsive to reflected light, wherein apparatus 10 comprises a control unit 20, a light source 30, a light receiver 40 and a support member 60. Each of light source 30 and light receiver 40 may be in communication with control unit 20. In one embodiment light source 30 outputs a broad band light, and in another embodiment light source 30 is a controllable light source responsive to control unit 20, particularly the wavelength of the light output by light source 30 is in such an embodiment responsive to an output of control unit 20. Control unit 20 may be implemented in dedicated circuitry, or by a general purpose computing platform arranged to perform computer readable instructions read from a non-transitory storage device. Multi-layer optical material structure 50 is disposed on support member 60 which is arranged to support multi-layer optical material structure 50 at a fixed location and angle relative to the output of light source 30. In an exemplary embodiment light exiting light source 30 impacts multi-layer optical material structure 50 at a near normal incidence, i.e. at about 90°+/−5% from a plane defined by the face of multi-layer optical material structure 50 opposing support member 60. Light receiver 40 is secured so as to receive light sourced by light source 30 reflected from multi-layer optical material structure 50 at a near normal incidence. In a non-limiting example light source 30 and light receiver 40 are provided as a single controllable optical block. In one non-limiting embodiment light receiver 40 comprises a lens. Control unit 20 comprises a processor 22 and a memory 25 in communication with each other. In one optional embodiment (not shown), light source 30 and light receiver 40 are placed within control unit 20 and are in optical communication with multi-layer optical material structure 50 via fiber optics. Control unit 20 may be distributed, for example, certain functions, as described below, may be performed by dedicated circuitry connected to light receiver 40, without exceeding the scope. As indicated above, control unit 20 may be a computer in communications with light source 30 and/or light receiver 40. In one embodiment (not shown) support member 60 comprises a translating mechanism. In one non-limiting embodiment, light source 30 is constituted of a tunable laser light, for example tunable over the range of 800-850 nanometers. In another embodiment, light source 30 is constituted of a broad range light source, such as a white light or a halogen lamp.

Figure 1B:
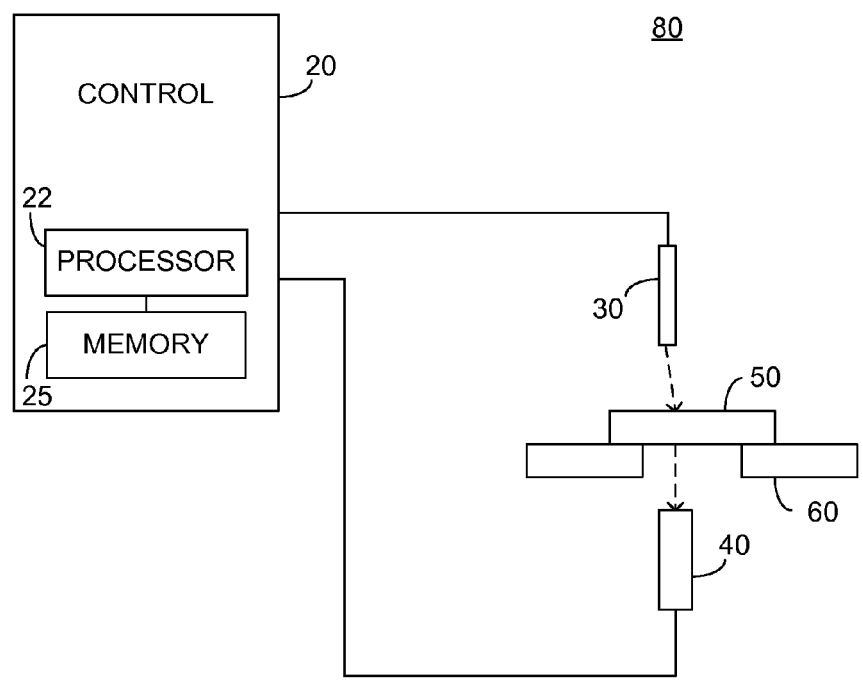
FIG. 1B illustrates a second embodiment of an apparatus arranged to determine at least one physical characteristic of a multi-layer optical material structure responsive to transmitted light.

FIG. 1B illustrates a second embodiment of an apparatus 80 arranged to determine at least one physical characteristic of a multi-layer optical material structure 50 responsive to transmitted light, wherein apparatus 80 comprises a control unit 20, a light source 30, a light receiver 40 and a support member 60. Each of light source 30 and light receiver 40 are preferably in communication with control unit 20, and the wavelength of the light output of light source 30 is in one embodiment responsive to an output of control unit 20. Multi-layer optical material structure 50 is disposed on support member 60 which is arranged to support multi-layer optical material structure 50 at a fixed location and angle relative to the output of light source 30. In an exemplary embodiment light exiting light source 30 impacts multi-layer optical material structure 50 at a near normal incidence, i.e. at 90°+/−5% from a plane defined by the face of multi-layer optical material structure 50 opposing support member 60. Light receiver 40 is secured so as to receive light sourced by light source 30 transmitted through multi-layer optical material structure 50 at a near normal incidence, preferably defined as 90°+/−5% from a plane defined by the face of multi-layer optical material structure 50 opposing support member 60. In one non-limiting embodiment light receiver 40 comprises a lens. Control unit 20 comprises a processor 22 and a memory 25 in communication with each other. In one optional embodiment (not shown), light source 30 and light receiver 40 are placed within control unit 20 and are in optical communication with multi-layer optical material structure 50 via fiber optics. Control unit 20 may be distributed, and certain functions, as described below, may be performed by dedicated circuitry connected to light receiver 40, without exceeding the scope. As indicated above, control unit 20 may be a computer, or other computing platform, in communications with light source 30 and/or light receiver 40. In one embodiment (not shown) support member 60 comprises a translating mechanism. In one non-limiting embodiment, light source 30 is constituted of a tunable laser light, for example tunable over the range of 800-850 nanometers. In another embodiment, light source 30 is constituted of a broad range light source, such as a white light or a halogen lamp.

In operation, control unit 20 of apparatus 80 is in all respects similar to control unit 20 whose operation will be described further hereinto below, with the exception that the transmitted light is utilized in place of reflected light.

Figure 2:
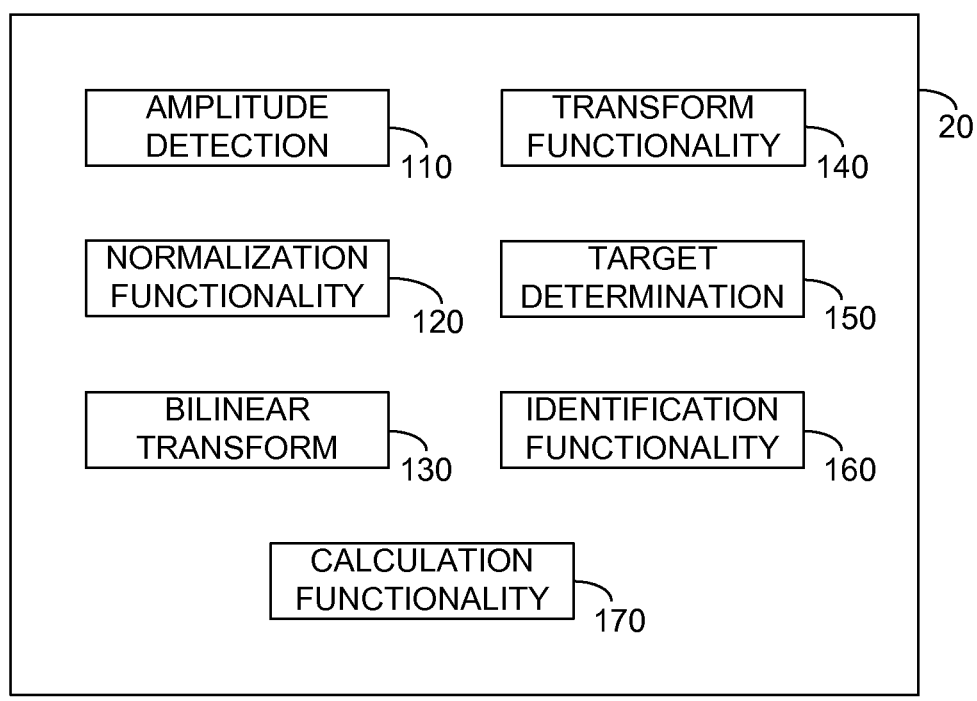
FIG. 2 illustrates a high level functional block diagram of an exemplary embodiment of a control unit of either FIG. 1A or FIG. 1B.

FIG. 2 illustrates a high level functional block diagram of an exemplary embodiment of control unit 20 of either FIG. 1A or FIG. 1B, comprising an amplitude detection functionality 110, an optional normalization functionality 120, a bilinear transform functionality 130, a transform functionality 140, a target peak determination functionality 150, an identification functionality 160 and a calculation functionality 170. Each of amplitude detection functionality 110, normalization functionality 120, bilinear transform functionality 130, transform functionality 140, target peak determination functionality 150, identification functionality 160 and calculation functionality 170 are preferably implemented as automated processes within processor 22 of control unit 20, instructions for the processes being stored on memory 25 in a machine readable format, preferably on a computer readable medium of fixed form, which may be a local storage drive, or may be remote storage drive accessed over a network connection. Alternatively, dedicated hardware may be provided for each, or some, of amplitude detection functionality 110, normalization functionality 120, bilinear transform functionality 130, transform functionality 140, target peak determination functionality 150, identification functionality 160 and calculation functionality 170 without exceeding the scope.

For ease of understanding, the operation of apparatus 10 of FIG. 1A will now be described in cooperation with the embodiment of control unit 20 of FIG. 2, it being understood that operation of apparatus 80 of FIG. 1B being in all respects similar. Light output by light source 30 is reflected from multi-layer optical material structure 50 and received at light receiver 40. In one embodiment, control unit 20 steps the wavelength of light output from light source 30 by discrete even intervals, and further determines, responsive to amplitude detection functionality 110, the amplitude of the reflected light. It is to be understood that stepping of the wavelength in discrete intervals is not meant to be limiting in any way, and sweeping of the wavelength may be performed, with samples taken at discrete intervals without exceeding the scope. In yet another embodiment, light source 30 continuously emits light in all desired spectra simultaneously. Light receiver 40 may use an internal grating, prism or other tuning means in order to perform the spectrometric conversion that will associate an amplitude with each discrete wavelength. In one embodiment, light receiver 40 is arranged to provide 2048 readings over the desired reflectance spectrum.

Control unit 20, preferably in communication with light receiver 40, detects the amplitude of light reflected from multi-layer optical material structure 50 as a function of the wavelength of the light output by light source 30. Control unit 20, responsive to optional normalization functionality 120, is further arranged to normalize the detected amplitude and preferably convert the measurements from wavelength to wave number for ease of calculation. The term wave number as utilized herein is defined as reciprocal of the wavelength, and is commonly used in spectroscopy, however this is not meant to be limiting in any way, and wavelength or frequency may be substituted, with the appropriate mathematical compensation, whenever the term wave number is utilized. The normalization equation is calculated based on the reflectance results measured for a known material with a known reflectance performance, such as aluminum, which has a reflectance of about 95%. A normalized value of the detected amplitude is thus calculated.

Control unit 20, responsive to bilinear transform functionality 130, is further arranged to perform a bilinear transform on the detected amplitudes as a function of wave number, with the term bilinear transform preferably defined as:

$$B[R(w)] = \frac{1 + R(w)}{1 - R(w)} \qquad \text{EQ. 1}$$

where R(w) is defined as the reflectance amplitude as a function of wave number. Preferably, the amplitudes are determined as a percentage of light output reflected.

Control unit 20 is further arranged, responsive to transform functionality 140, to transform the bilinear transformed reflectance amplitudes to the optical thickness domain, preferably by performing a Fourier transform, even further preferably by performing a fast Fourier transform. There is no limitation to the transform, and autocorrelation or covariance methods may be used to determine optical thickness and amplitude relationships without limitation. In an exemplary embodiment a Fourier transform is performed by transform functionality 140, wherein the data is interpolated at equi-spaced wave-number points, high-pass filtered, windowed, zero padded to a specific number of points and a fast Fourier transform (FFT) algorithm is applied.

The term optical thickness is defined as two times the refractive index times the thickness, denoted "2nd", wherein "n" denotes the refractive index and "d" denotes the thickness of the layer. Control unit 20, is in one embodiment further provided with target information regarding multi-layer optical material structure 50, i.e. the target layer thickness and refractive index of each layer, and is arranged, responsive to target determination functionality 150, to determine expected amplitude and optical thickness of peaks which are representative of single actual layer interfaces. In particular, and as will be described further hereinto below, the bilinear transformed reflectance amplitudes transformed to the optical thickness domain exhibit a plurality of peaks, only some of which are associated with single actual layer interfaces. Other peaks are associated with multiple reflectance paths, and thus are not associated with a single actual layer interface. Control unit 20 thus determines amplitudes and optical thickness of the expected peaks associated with single actual layer interfaces from target structure data.

In another embodiment, as described further below in relation to FIG. 6, control unit 20 monitors production in-situ of multi-layer optical material structure 50, and extracts the refractive index and layer thickness without requiring target information.

Control unit 20, in cooperation with identification functionality 160, and responsive to target determination functionality 150, is arranged to identify the actual peaks from the bilinear transformed reflectance amplitudes transformed to the optical thickness domain which are associated with single actual layer interfaces.

Control unit 20 is further arranged, in cooperation with calculation functionality 170, to calculate at least one physical characteristic of multi-layer optical material structure 50 responsive to the identified actual peaks. In one embodiment at least one layer thickness is determined. In another embodiment the refractive index of at least one layer is determined. In one embodiment the physical characteristic of the top layer is calculated, and in another embodiment further information is provided regarding previously developed layers.

In the embodiment where support member 60 is translatable, support member 60 is translated in a predetermined pattern. A "cross section" graph, or a two-dimensional representation of at least one physical characteristic of multi-layer optical material structure 50 is thereby calculated, as described above.

Figure 3A:
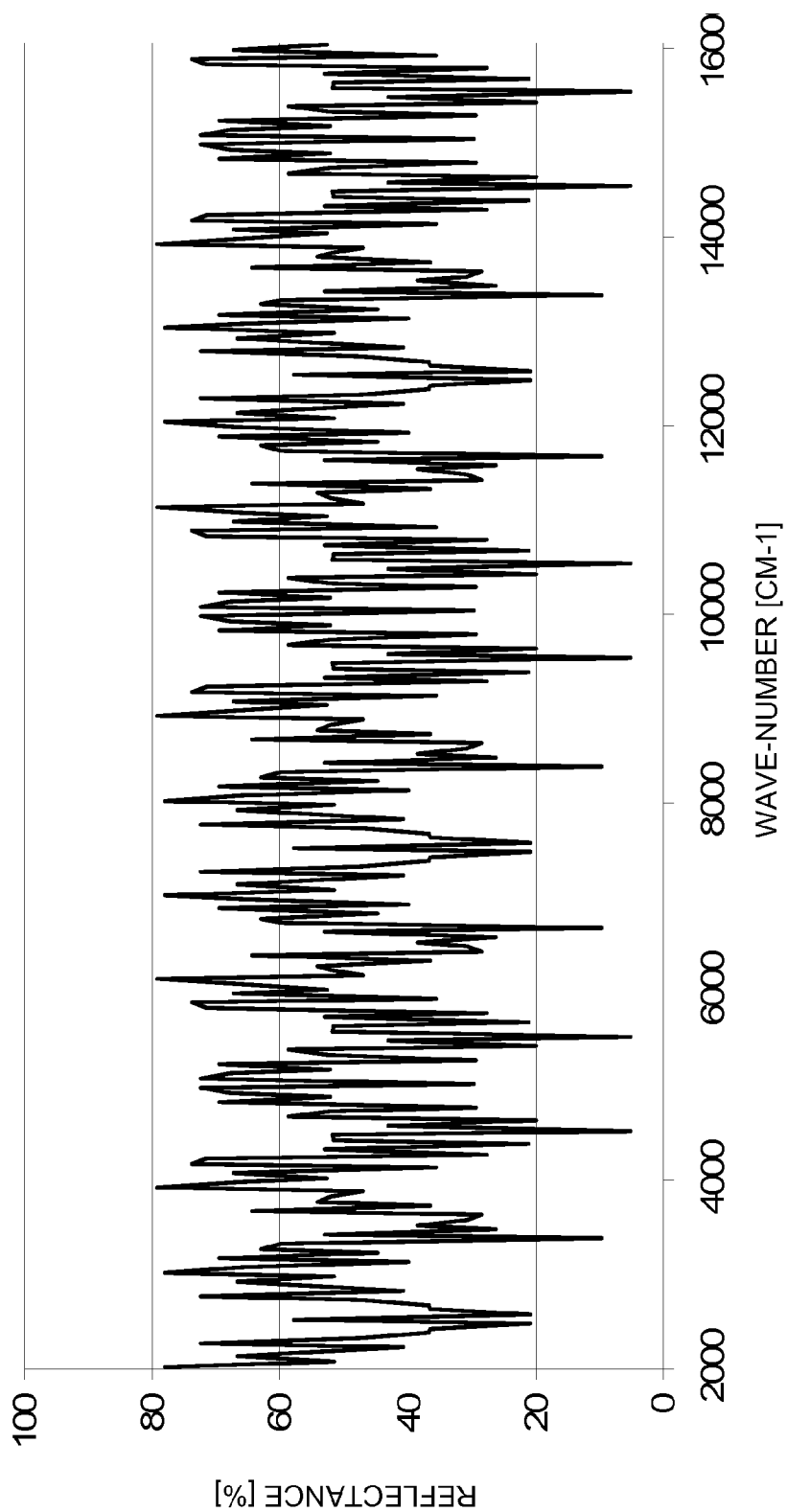
FIG. 3A illustrates a plot of reflectance data vs. wave number of a 3 layer sample with large refractive index steps between the layers.
Figure 3B:
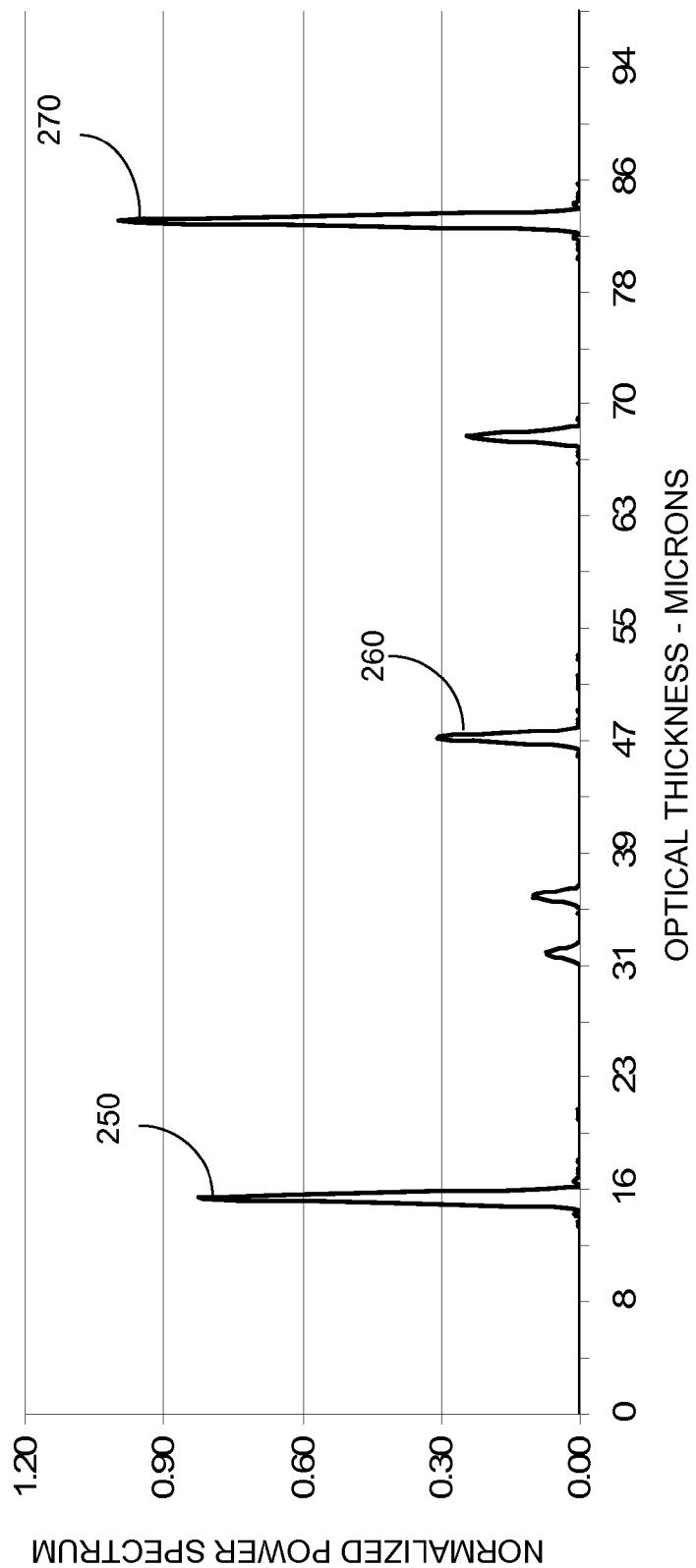
FIG. 3B illustrates a plot of the reflectance data of FIG. 3A after performing a bilinear transform and a Fourier transform to the optical thickness domain.

In further explanation, FIG. 3A illustrates a plot of reflectance data vs. wave number of a 3 layer sample with large refractive index steps between the layers, in particular the steps are greater than 20%, wherein the x-axis reflects wave number expressed in $cm^{-1}$ and the y-axis represents the percentage of total light output by light source 30 received by light receiver 40. FIG. 3B illustrates a plot of the reflectance data of FIG. 3A after performing the bilinear transform of EQ. 1, responsive to bilinear transform functionality 130, and a Fourier transform to the optical thickness domain, responsive to transform functionality 140. The x-axis of FIG. 3B reflects optical thickness expressed in microns (μm) and the y-axis represents the normalized power spectrum. The plot of FIG. 3B shows 6 different peaks for the 3 layer sample, and thus identification of the peaks associated with single actual layer interfaces is required. Responsive to target determination functionality 150 and identification functionality 160, the peaks associated with single actual interfaces are determined and identified as peaks 250, 260 and 270.

In yet further detail, for a multi-layer structure, with the assumption of near normal incidence, negligible absorption and dispersion in the utilized wave-number range and small refractive index steps between layers, defined herein as refractive index steps of less than or equal to about 20%, an analytical approximation for the bilinear transformed reflectance, as written in EQ. 1 is:

$$B\{R(w)\} = B_0 + B_1 \sum_{j=1}^{N} \left(\frac{n_{j+1}-n_j}{n_s}\right) \cos\left(4\pi \sum_{i=1}^{j} n_i d_i w\right) \qquad \text{EQ. 2}$$

where $n_j$ is the refractive index of layer j, and $d_j$ is the thickness of layer j. $B_0$ and $B_1$ are constants, N is the number of layers, w is the wave-number and $n_s$ is the refractive index of the substrate and is equivalent to $n_{j+1}$ when j=N. In some detail, EQ. 2 can be derived by applying flow-graph analysis for the calculation of reflectivity "r" of the various layers, with "r" express as a function of the Fresnel coefficients of the interfaces ($r_{q,q+1}$) in a manner taught by G. E. Aizenberg, P. L. Swart and B. M. Lacquet, in Optical Eng. 33 (9), 2886 (1994), the entire contents of which is incorporated herein by reference. The reflectance R for each structure is then calculated by multiplying the reflectivity "r" by its complex conjugate r*. The bilinear transformation of EQ. 1 is then applied to the reflectance R, so an expression that is a sum of components is achieved. The amplitude of each component is affected by products of Fresnel coefficients $r_{q,q+1}$. By considering that $r_{q,q+1}<1$, the bilinear transformed reflectance is approximated by neglecting second and higher order terms. As will be described further below in relation to EQ. 6, the Fresnel coefficients are replaced by their refractive indices expressions. From the results of a succession of layers, i.e. 1 layer, 2 layers, 3 layers and further, the general expression of EQ. 2 in series form is derived.

From EQ. 2 it is evident that the Fourier analysis of B(w) leads to a spectrum in the optical thickness domain, denoted variously and interchangeably as θ, or as described above as "2nd", i.e. 2 times the refractive index times the layer thickness, with the factor of 2 added to take into account that light must pass through the layer in both directions for reflectance data. Hence, we can write the term cos(4π·n·d·w) appearing in EQ. 2 as cos(2π·θ·w).

It is to be understood that for transmittance measurements, as described in relation to apparatus 80 of FIG. 1B, the change in light flow is to be taken into account, and the transform to be performed is not the bilinear transformation of EQ. 1 but a 2/T transform as will be described further. The position of the peaks corresponds directly to the interfaces between layers.

In further clarification, cos(2π·θ·w) is similar in form to the oscillatory function cos(2π·f·t), with "w", wave number, replacing "t" and θ replacing "f". So for an expression in the wave number domain, the spectrum will be in the θ domain, and the "equivalent frequency" of each "spectral line" will be 2*n*d.

For large refractive index steps, defined herein as refractive index steps greater than or equal to 20% between adjacent layers, an analytical approximation for the bilinear transformed reflectance is:

$$B^{(N)} = B^0 \left(1 + \sum_{k=1}^{N} \sum_{p=1}^{N-k+1} B_p^k \cos 4\pi \sum_{m=p}^{p+k-1} n_m d_m w \right) \qquad \text{EQ. 3}$$

where the k-superscript (at the B coefficients) indicates groups of "k adjacent layers". It is to be noted that EQ. 3 may also be used for refractive index steps of less than 20% between adjacent layers. EQ. 3 is derived in a manner similar to the derivation of EQ. 2 described above, noting that since $r_{q,q+1}<1$ the bilinear transformed reflectance is approximated by neglecting only third and higher order terms. Second order terms are included. A general expression in series form is derived from the results of 1, 2, 3 and more layers. The p-subscript indicates the starting layer for each group, i.e. the layer for which light first interacts with the group, i.e. the last layer of the group which has been formed. The concept of groups of layers can be seen by means of the 3 layers example seen in FIG. 4C. Here "k" can be 1, 2 or 3. We have three groups of one layer (k=1): layer 1, with physical characteristics $d_1$ and $n_1$; layer 2 with physical characteristics $d_2$ and $n_2$; and layer 3 with physical characteristics $d_3$ and $n_3$. We have two groups of two adjacent layers (k=2): the group of layer 1 and layer 2; and the group of layer 2 and layer 3. We have one group of three adjacent layers (k=3), i.e. the group of layer 1, layer 2 and layer 3. Thus, for the group of layer 2 and layer 3 we have p=2 because 2 is the starting; for the group of layer 1, layer 2 and layer 3, p=1 because 1 is the starting layer.

EQ. 3 is composed of certain elements, in particular:

$$B_p^k = \frac{4 r_{p-1,p} \cdot r_{p+k-1,p+k}}{\prod_{q=p}^{p+k}(1+r_{q-1,q}^2)} \qquad \text{EQ. 4}$$

$$B^0 = \prod_{q=1}^{N+1} \frac{1+r_{q-1,q}^2}{1-r_{q-1,q}^2} \qquad \text{EQ. 5}$$

Where the (Fresnel) reflectivity coefficient between layers q−1 and q is given by:

$$r_{q-1,q} = \frac{n_{q-1} - n_q}{n_{q-1} + n_q} \qquad \text{EQ. 6}$$

where $n_0$ and $n_{N+1}$ are the refractive indices of air and substrate ($n_s$), respectively. Note that EQ. 3-EQ. 5 are also valid for small refractive index steps. The product $B^0 \cdot B_p^{k+1}$ represents the amplitude of each of the "spectral lines" that we have in the optical thickness domain. It is inferred from EQ. 3, responsive to the two outer summations, that the number of observed spectral peaks "M" is given by:

$$M = \sum_{j=1}^{N} j \qquad \text{EQ. 7}$$

where N peaks that correspond to layers interfaces, should be identified for measuring the layers thicknesses; the rest (M−N peaks) should be ignored or considered spurious. By measuring the amplitude of the peaks and using EQ. 4-EQ. 6 it is also possible to estimate the refractive indices as will be described further below.

The interface components, i.e. reflections from a single interface, from EQ. 3 are described below, where EQ. 8 represents the spectral component of peak "k" and EQ. 9B represents the amplitude of the peak:

$$B^0 B_1^k \cos 4\pi \sum_{m=1}^{k} n_m d_m w \qquad \text{EQ. 8}$$

$$B_1^k = \frac{4 r_{0,1} \cdot r_{k,k+1}}{\prod_{q=1}^{k+1}(1+r_{q-1,q}^2)} \qquad \text{EQ. 9A}$$

It is to be noted that the amplitude of peak "k" is thus:

$$C_1^k = B^0 B_1^k \qquad \text{EQ. 9B}$$

with k=1, 2, 3 ... N.

The above analysis has been detailed in regards to apparatus 10 of FIG. 1A, however this is not meant to be limiting in any way. A similar analysis may be performed with apparatus 80 of FIG. 1B utilizing the received transmittance data wherein transmittance as a function of wavelength is denoted T(w). The bilinear transform of EQ. 1 is not required, and instead the function 2/T(w) is substituted for B(w) in each of EQ. 2 to EQ. 9. In some detail, the transformation for transmittance derives form the fact that with the assumption of no absorption:

$$R+T=1 \qquad \text{EQ. 9C}$$

Taking into account EQ. 9C, and substituted in EQ. 1 we can achieve:

$$R = \frac{B-1}{B+1} \qquad \text{EQ. 9D}$$

and combining EQ. 9C and EQ. 9D:

$$B = \frac{2}{T} - 1 \qquad \text{EQ. 9E}$$

For spectral analysis the constant of −1 can be neglected.

Description of an Exemplary 3 Layer Growth Process

Figure 4A:
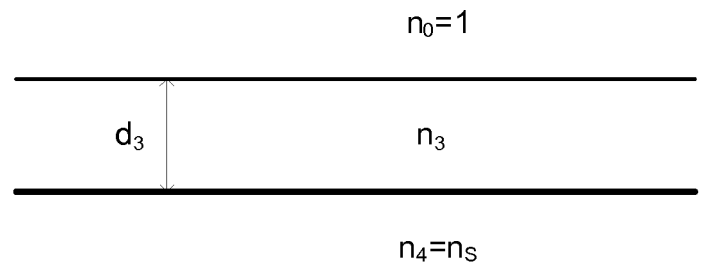
FIG. 4A-4C illustrate steps in the formation of a multi-layer optical material structure.
Figure 4B:
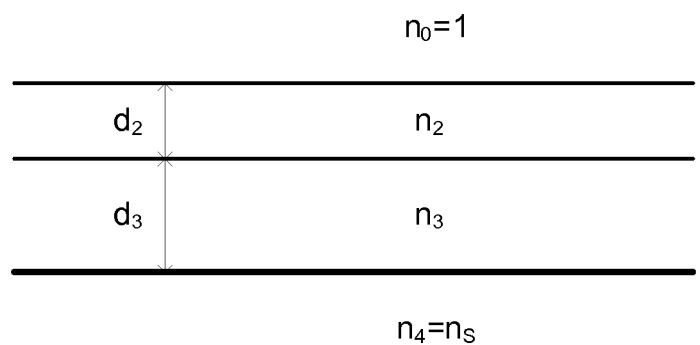
Figure 4C:
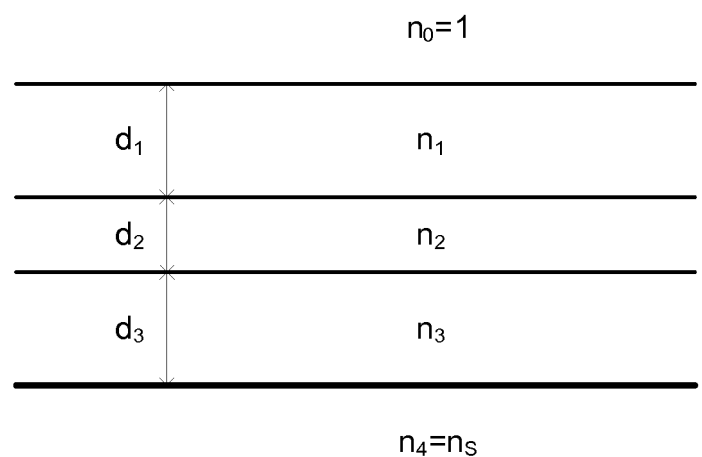

Referring now to FIGS. 4A-4C a 3 layer growth process will be described in relation to apparatus 10 of FIG. 1. Layers of multi-layer optical material structure 50 are grown on a substrate, one on top of the other. The layer grown directly on the substrate is denoted herein layer 3, with layer 2 grown on top of layer 3, and layer 1 grown on top of layer 2.

In particular, referring to FIG. 4A, layer 3 has been grown on the substrate. The substrate exhibits a refractive index denoted $n_s$, layer 3 exhibits a thickness denoted $d_3$ and a refractive index denoted $n_3$. Above layer 3 is air, which exhibits a refractive index of 1, denoted $n_0$. In accordance with EQ. 3-EQ. 6, a bilinear transformation of the reflectance shows only a single spectral component as:

$$C_1^1 * \cos 4\pi w(n_3 d_3) \qquad \text{EQ. 10}$$

Where its amplitude is defined by:

$$C_1^1 = \frac{4 r_{03} \cdot r_{34}}{(1-r_{03}^2)(1-r_{34}^2)} = \frac{(1-n_3^2)(n_3^2-n_S^2)}{4 n_3^2 n_S} \qquad \text{EQ. 11}$$

Note that:

$$C_1^1 = B^0 B_1^1 \qquad \text{EQ. 11A}$$

Referring to FIG. 4B, a second layer, denoted layer 2, has now been grown directly on layer 3 of FIG. 4A. The substrate exhibits a refractive index denoted $n_s$, layer 3 exhibits a thickness denoted $d_3$ and a refractive index denoted $n_3$, layer 2 exhibits a thickness denoted $d_2$ and a refractive index denoted $n_2$, and above layer 2 is air, which exhibits a refractive index of 1, denoted $n_0$. In accordance with EQ. 3 the spectrum of the bilinear transformed Reflectance shows three spectral components, given by:

$$C_1^1 * \cos 4\pi w(n_2 d_2) \qquad \text{EQ. 12}$$

$$C_2^1 * \cos 4\pi w(n_3 d_3) \qquad \text{EQ. 13}$$

$$C_1^2 * \cos 4\pi w(n_2 d_2 + n_3 d_3) \qquad \text{EQ. 14}$$

where $C_1^1$ and $C_1^2$ are amplitudes of interface peaks, in particular $C_1^1$ is the last layer grown, $C_1^2$ is the actual interface between layer 3 and the substrate, while $C_2^1$ is the amplitude of a spurious peak. In particular, interface peaks are those that are located at positions that are coincident with interfaces between materials, while other peaks are not of interest as they do not represent actual interfaces. The amplitude of the interface peaks can be directly calculated by means of EQ. 5, 6, 8 AND 9 as EQ. 15 and EQ. 16, respectively.

$$C_1^1 = \frac{4 r_{02} \cdot r_{23}(1+r_{34}^2)}{(1-r_{02}^2)(1-r_{23}^2)(1-r_{34}^2)} = \frac{(1-n_2^2)(n_2^2-n_3^2)(n_3^2+n_S^2)}{8 n_2^2 n_3^2 n_S} \qquad \text{EQ. 15}$$

$$C_1^2 = \frac{4 r_{02} \cdot r_{34}}{(1-r_{02}^2)(1-r_{23}^2)(1-r_{34}^2)} = \frac{(1-n_2^2)(n_2+n_3)^2(n_3^2-n_S^2)}{16 n_2^2 n_3^2 n_S} \qquad \text{EQ. 16}$$

In further clarification, EQ. 3 is a general expression providing the amplitudes of all interface peaks and non-interface, or spurious, peaks. EQ. 8, in cooperation with EQ. 5, 6 and 9 only provides information regarding the actual interface peaks.

Referring to FIG. 4C, a third layer, denoted layer 1, has now been grown directly on layer 2 of FIG. 4A. The substrate exhibits refractive index $n_s$, layer 3 exhibits thickness $d_3$ and refractive index $n_3$, layer 2 exhibits thickness $d_2$ and refractive index $n_2$, layer 1 exhibits a thickness denoted $d_1$ and a refractive index denoted $n_1$, and above layer 1 is air, which exhibits a refractive index of 1, denoted $n_0$. In accordance with EQs. 3-6 the spectrum of the bilinear transformed reflectance shows six spectral components, given by:

$$C_1^1 * \cos 4\pi w(n_1 d_1) \qquad \text{EQ. 17}$$

$$C_2^1 * \cos 4\pi w(n_2 d_2) \qquad \text{EQ. 18}$$

$$C_3^1 * \cos 4\pi w(n_3 d_3) \qquad \text{EQ. 19}$$

$$C_1^2 * \cos 4\pi w(n_1 d_1 + n_2 d_2) \qquad \text{EQ. 20}$$

$$C_2^2 * \cos 4\pi w(n_2 d_2 + n_3 d_3) \qquad \text{EQ. 21}$$

$$C_1^3 * \cos 4\pi w(n_1 d_1 + n_2 d_2 + n_3 d_3) \qquad \text{EQ. 22}$$

whereas only the three components of EQ. 17, 20 and 22 represent single interface reflections. In further detail, EQ. 17 represents the interface of the last layer grown, EQ. 20 represents the position of the interface between layers 2 and 3, and EQ. 22 represents the position of the interface between layer 3 and the substrate. The amplitudes calculated from Equations (5), (6), (8) and (9) are:

$$C_1^1 = \frac{4r_{01} \cdot r_{12}(1+r_{23}^2)(1+r_{34}^2)}{(1-r_{01}^2)(1-r_{12}^2)(1-r_{23}^2)(1-r_{34}^2)} = \frac{(1-n_1^2)(n_1^2-n_2^2)(n_2^2+n_3^2)(n_3^2+n_S^2)}{16n_1^2 n_2^2 n_3^2 n_S} \quad \text{EQ. 22}$$

$$C_1^2 = \frac{4r_{01} \cdot r_{23}(1+r_{34}^2)}{(1-r_{01}^2)(1-r_{12}^2)(1-r_{23}^2)(1-r_{34}^2)} = \frac{(1-n_1^2)(n_1+n_2)^2(n_2^2-n_3^2)(n_3^2+n_S^2)}{32n_1^2 n_2^2 n_3^2 n_S} \quad \text{EQ. 23}$$

$$C_1^3 = \frac{4r_{01} \cdot r_{34}}{(1-r_{01}^2)(1-r_{12}^2)(1-r_{23}^2)(1-r_{34}^2)} = \frac{(1-n_1^2)(n_1+n_2)^2(n_2+n_3)^2(n_3^2-n_S^2)}{64n_1^2 n_2^2 n_3^2 n_S} \quad \text{EQ. 24}$$

Refractive Index Calculation

The refractive index of each layer in the growth process can be measured by knowing the refractive indices of the substrate and all of the previously deposited layers. In particular, to determine the refractive index of the last layer grown, we preferably utilize the amplitude of the first interface peak, or the lowest optical thickness, which is inferred from EQ. 8 and EQ. 9. In some further detail, EQ. 8 shows only components reflective of actual interfaces. EQ. 9A multiplied by EQ. 5 enables a calculation of the amplitude of each interface component.

In further detail, and with reference to the exemplary 3 layer growth process described above, given an "N" layer structure, the refractive index of each layer, denoted layer "i", can be calculated from:

$$n_i^2 = \frac{-\beta_i + \sqrt{\beta_i^2 - 4n_{i+1}^2}}{2} \quad \text{EQ. 25}$$

where $\beta_i$ is defined as:

$$\beta_i = \frac{C_1^1[i]}{\alpha_i} - n_{i+1}^2 - 1 \quad \text{EQ. 26}$$

where $C_1^1[i]$ is the amplitude of the first interface peak for the layer in process "i" and $\alpha_i$ is given by:

$$\alpha_i = \frac{1}{4n_S} \quad \text{For } i = N \quad \text{EQ. 27}$$

$$\alpha_i = \frac{\alpha_{i+1}}{2}\left(1 + \frac{n_{i+2}^2}{n_{i+1}^2}\right) \text{ For } i = 1, 3, 4 \ldots (N-1) \quad \text{EQ. 28}$$

In order to calculate the refractive index of each layer, an exemplary embodiment of a procedure is as follows:

1. For the first layer in the process, calculate $\alpha_N$ and $\beta_N$ by means of EQ. 26 and EQ. 27. Use for $C_1^1$ the amplitude of the only peak observed at the spectrum, since at the first layer only a single reflected peak is observed.
2. Calculate $n_N^2$ according to EQ. 25 and get $n_N$.
3. For the second layer in process calculate $\alpha_{N-1}$ and $\beta_{N-1}$ responsive to EQ. 26 and EQ. 28. Use for $C_1^1$ the amplitude of the spectral interface peak in the optical thickness domain exhibiting the smallest optical thickness.
4. Calculate $n_{N-1}^2$ according to EQ. 25 and get $n_{N-1}$.
5. For each additional layer repeat steps 3 and 4.

In further clarification of the above process:
"N" is the first deposited layer, i.e. the layer deposited or grown directly on the substrate. The layer above the first deposited layer is thus denoted "N−1". The last layer deposited in the structure is layer 1. Therefore, for i=N we have that $n_{i+1} = n_S$ Mathematically, the values of $C_1^1$ can be positive or negative. For each calculation of a layer refractive index both positive and negative values are to be considered. If one of the signs leads to a calculation of an imaginary "$n_i$", the opposite sign for $C_1^1$ is adopted. In the event that both signs of $C_1^1$ lead to real values of refractive index, i.e. non-imaginary values, the appropriate value is to be selected based on expected refractive index values, input as part of the process parameters.

Our spectrum figures show the "Normalized Power Spectrum", the amplitude of $C_1^1$ should preferably thus be calculated by using the square-root of the power spectrum before normalization.

The calculation of refractive index according to EQ. 25-28 is based on the calculation of the refractive index of the previously generated layer.

Distinguishable Thickness

The minimum layer thickness that can be resolved is given by the range of the reflectance data and the characteristics of the material, and is denoted:

$$2nd_{MIN} = (w_{MAX} - w_{MIN})^{-1} \quad \text{EQ. 29}$$

In a non-limiting embodiment in which the wave number range is from 2000 to 16000 cm$^{-1}$, for n=5 the minimum thickness will thus be 72 nm. The maximum optical thickness which can be resolved will depend on the wave-number resolution of the measurement equipment, denoted $\Delta w$, and aliasing considerations, and is in accordance with:

$$\left(2\sum_{j=1}^{N} n_j d_j\right)_{MAX} = \frac{\Delta w^{-1}}{2} \quad \text{EQ. 30}$$

In a non-limiting example in which the average refractive index of a multi-layer-structure is n=3 and $\Delta w$=10 cm$^{-1}$; we will be able to measure a maximum optical thickness of 0.5 mm and a depth of ~80 µm. The maximum and minimum wave-numbers can be limited by equipment and by characteristics of the material. For example, at what wave-number we stop considering negligible absorption and dispersion for a given material. From EQ. 29 it is clear that the minimum optical thickness $\theta_{min}$ is a function of $w_{max}$ and $w_{min}$; but for the minimum thickness we have to do $\theta_{min}/(2 \cdot n)$, where "n" depends on the material.

Figure 5:
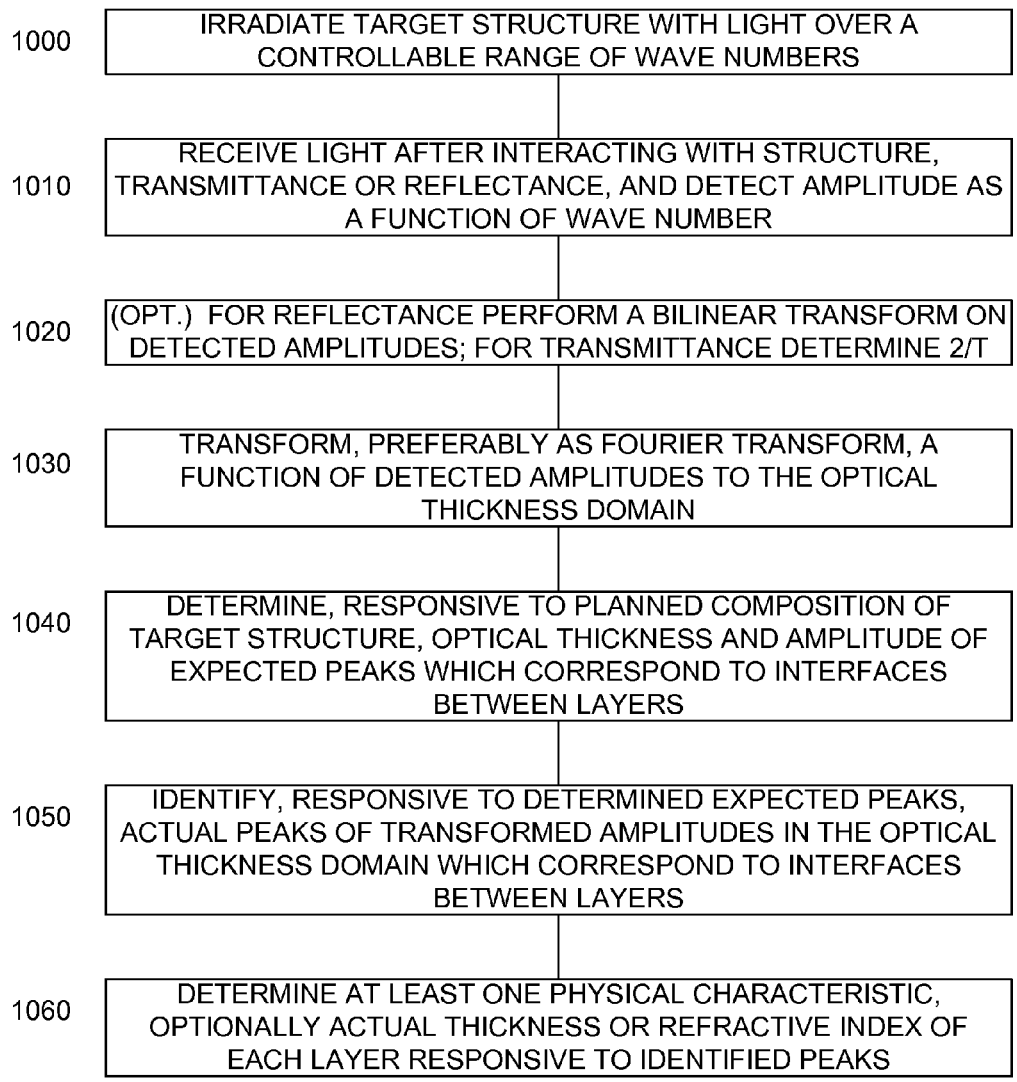
FIG. 5 illustrates a high level flow chart of the operation of the apparatus of either FIG. 1A or FIG. 2B to determine actual thickness or refractive index of a layer.

FIG. 5 illustrates a high level flow chart of the operation of the apparatus of either FIG. 1A or FIG. 2B, and in particular control unit 20, to determine actual thickness or refractive index of a layer. In stage 1000, a target structure is irradiated with light over a range of wavelengths. In stage 1010, the light of stage 1000 is received after interacting with the target structure, either by reflectance as described above in relation to apparatus 10 or by transmittance as described above in relation to apparatus 80. The amplitude of the detected light as a function of the wavelength is input to control unit 20, optionally normalized and further preferably converted to amplitude, optionally normalized, as a function of wave number. As indicated above the term wave numbers is used as a commonly expressed format for frequency or wavelength without limitation. In stage 1020, a bilinear transform is optionally performed by control unit 20 of apparatus 10, as described above in relation to EQ. 1. For control unit 20 of apparatus 80, a transform is optionally performed by control unit 20 of apparatus 80, as described above in relation to EQ. 1 with substitution of function $2/T(w)$ for $B(w)$ as described in EQ. 9D.

In stage 1030, the amplitudes of stage 1010, optionally transformed by stage 1020, are further transformed to the optical thickness domain, and all peaks of the transform are identified. Preferably, the transform of stage 1030 is a Fourier transform, further preferably implemented as an FFT.

In stage 1040, responsive to an input planned composition of the target structure of stage 1000, the expected optical thickness and amplitude of peaks associated with single interface between layers is determined, responsive to EQ. 3-9, described above. In stage 1050, responsive to the expected optical thickness and amplitude peaks of stage 1040, the actual peaks of stage 1030 associated with single interfaces between layers, are identified. In one embodiment the amplitudes are used as a leading indicator, and in another embodiment optical thickness is used as a leading indicator. In yet another embodiment a combination of amplitudes and optical thickness values are used to determine the actual peaks. In yet another embodiment, if the total number of actual peaks is greater than the maximal expected number of peaks calculated in step 1040, the system outputs an error signal or visual indicator advising that an extra parasitic layer, or layers, has been formed.

In yet another embodiment, as consecutive layers are grown or deposited, the peaks of the actual interfaces shift to deeper optical depth with each growth step. The balance of the peaks, which do not shift with each consecutive layer are thus identified as non-interface peaks.

In stage 1060, at least one physical characteristic of the last layer is determined responsive to the identified peaks of stage 1050. Preferably the actual thickness of the layer is determined, the actual thickness determined in accordance with:

$$d = \theta/2n \qquad \text{EQ. 31}$$

with n being the planned refractive index of the layer. Alternately, the calculated refractive index is derived as described in connection with Eq. 25-28 which enables the calculation of each layer refractive index based on the amplitude of the interface peak.

Thus, the method of FIG. 5 determines the actual thickness and/or the actual refractive index of a top layer of a multi-layer optical material structure having large refractive index steps, responsive to design criteria and light irradiation.

Figure 6:
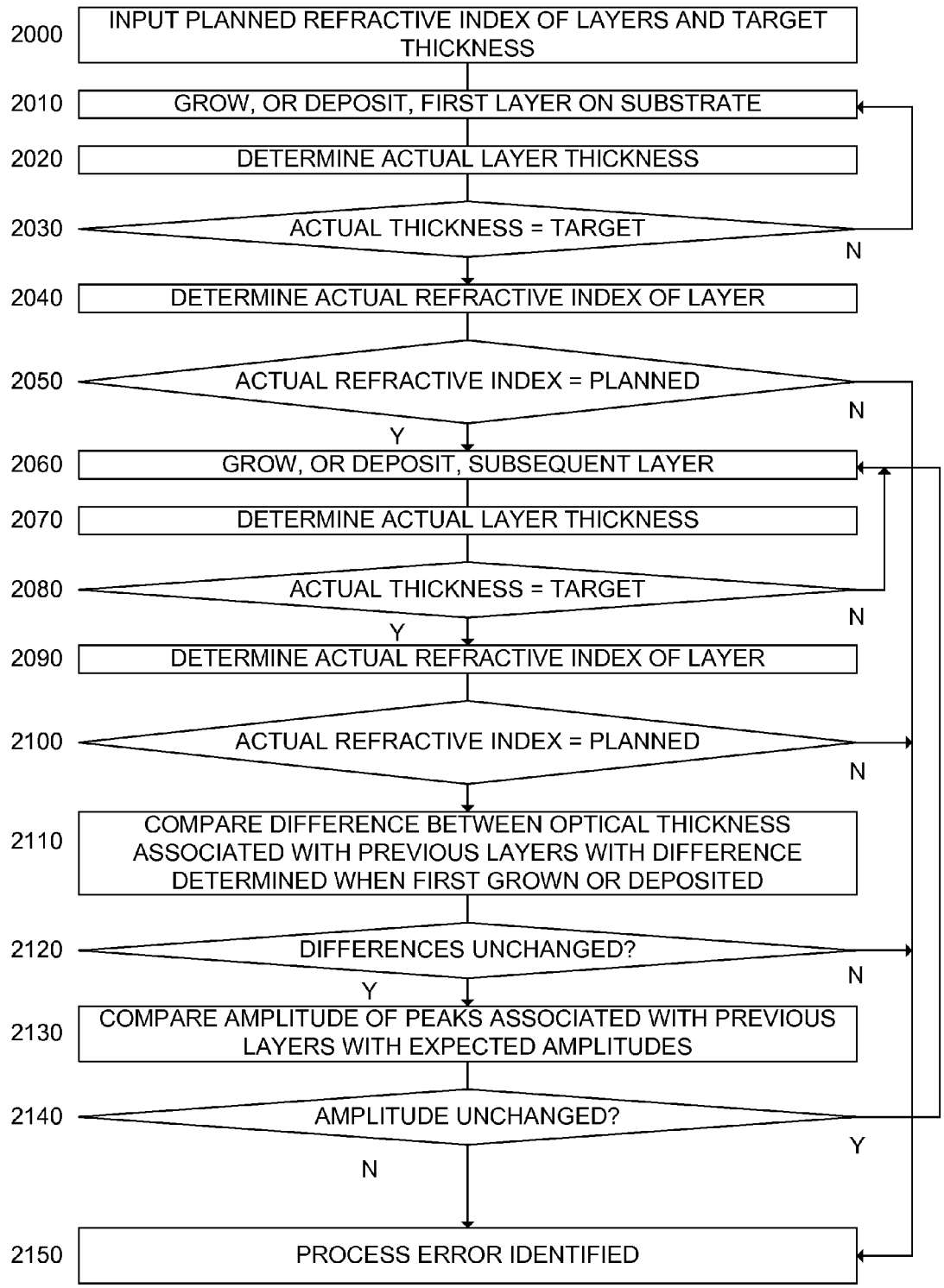
FIG. 6 illustrates a high level flow chart of the operation of the apparatus of either FIG. 1A or FIG. 2B to determine actual thickness or refractive index of layers in a process, and to further determine process errors.

FIG. 6 illustrates a high level flow chart of the operation of the apparatus of either FIG. 1A or FIG. 2B to determine actual thickness or refractive index of layers in a process, and to further determine process errors. In stage 2000, the planned refractive index and target thickness of each of the layers to be deposited, or grown, is input. In stage 2010, a first layer is grown, or deposited, on the substrate. In stage 2020, the actual thickness of the layer is determined, as described above in relation to FIG. 5. In stage 2030 the actual thickness of the layer is compared to the target thickness. In the event that the actual thickness is less than the target thickness, stage 2010 is continued. It is to be understood that stages 2020 and 2030 may be performed at predetermined intervals, or responsive to process flow stages, or benchmarks, without limitation. The amplitude and optical thickness of the identified peaks, as described above in relation to FIG. 5, are preferably stored in memory 25.

In the event that in stage 2030 the actual thickness is equal to the target thickness of stage 2000, within acceptable variances, in stage 2040 the actual refractive index of the layer of stage 2010 is determined, as described above in relation to FIG. 5. In stage 2050 the determined actual refractive index, is compared with the target refractive index, as described above in relation to FIG. 5. In the event that the determined refractive index is not equal to the target refractive index of stage 2000, within acceptable variances, in stage 2150 a process error is determined. Preferably an error signal is output to an operator indicating the error, with details of the determined actual thickness and refractive index, for process correction.

In the event that in stage 2050 the determined refractive index is equal to the target refractive index of stage 2000, within acceptable variances, in stage 2060 a subsequent layer is grown or deposited. In stage 2070, the actual thickness of the subsequent layer of stage 2060 is determined, as described above in relation to FIG. 5. In stage 2080 the actual thickness of the subsequent layer determined in stage 2070 is compared to the target thickness of stage 2000. In the event that the actual thickness is less than the target thickness, stage 2060 is continued. It is to be understood that stages 2070 and 2080 may be performed at predetermined intervals, or responsive to process flow stages, or benchmarks, without limitation. The amplitude and optical thickness of the identified peaks, as described above in relation to FIG. 5, are preferably stored in memory 25.

In the event that in stage 2080 the actual thickness of the subsequent layer of stage 2060 is equal to the target thickness of stage 2000, within acceptable variances, in stage 2090 the actual refractive index of the subsequent layer of stage 2060 is determined, as described above in relation to FIG. 5. In stage 2100 the determined actual refractive index of stage 2090 is compared with the target refractive index of stage 2000, as described above in relation to FIG. 5. In the event that the determined refractive index is not equal to the target refractive index of stage 2000, within acceptable variances, in stage 2150 a process error is determined and an output signal is preferably generated, as described above.

In the event that in stage 2100 the determined refractive index of the subsequent layer is equal to the target refractive index of stage 2000, within acceptable variances, in stage 2110 the difference in optical thickness between identified peaks of previous layers is compared with the stored difference in optical thickness for the previous layers. In stage 2120, in the event that the difference between the optical thickness of previous layers is not the same as the stored difference, in stage 2150 a process error is determined and an output signal is preferably generated, as described above. In an exemplary embodiment, the change in optical thickness is indicative of a shift in the interface between materials, which may be an indication of an unwanted interlayer diffusion process taking place. There is no requirement that stages 2110-2120 be performed before stages 2130-2140, and the reverse order is specifically contemplated.

In the event that in stage 2120 the difference between the optical thickness of previous layers is the same as the stored difference, in stage 2130 the amplitude of the peaks related to interfaces is compared with a computed target value which is calculated using EQ. 5, 6, 8 and 9. In stage 2140, in the event that the amplitude of the peaks in the optical thickness domain has changed from the expected amplitudes, in stage 2150 a process error is determined and an output signal is preferably generated, as described above. In an exemplary embodiment, the change in amplitude from the expected values is indicative of inter-layer diffusion. In the event that in stage 2140 the amplitudes of the peaks in the optical thickness domain remain within a predetermined range from a target value stage 2060 is again performed as described above.

Thus, the method of FIG. 6 identifies process errors caused by changes in previous layers, previous interfaces, and inappropriate refractive indexes, in a non-destructive continuous manner or at predetermined measurement intervals.

Stages 2110-2140 are further explained in relation to FIGS. 7A-7D and the tables below for the production of a 4 layer sample. TABLE I represents the layers of the target structure, with layer 4 being grown directly on the substrate, and layer 1 being the top layer, i.e. the last layer to be grown.

TABLE I

| LAYER | REFRACTIVE INDEX | THICKNESS μm |
|---|---|---|
| Substrate | 3.45 | |
| 4 | 5 | 1 |
| 3 | 7 | 1.2 |
| 2 | 5 | 1.4 |
| 1 | 4 | 1 |
| AIR | 1 | |

TABLE II represents the position of the interface peaks for each growth step for the layers of TABLE I.

TABLE II

| INTERFACE LAYER | 1 | 2 | 3 | 4 |
|---|---|---|---|---|
| | OPTICAL THICKNESS μm | | | |
| 4 | 10.0 | | | |
| 3 | 16.8 | 26.8 | | |
| 2 | 14.0 | 30.8 | 40.8 | |
| 1 | 8.0 | 22.0 | 38.8 | 48.8 |

Figure 7A:
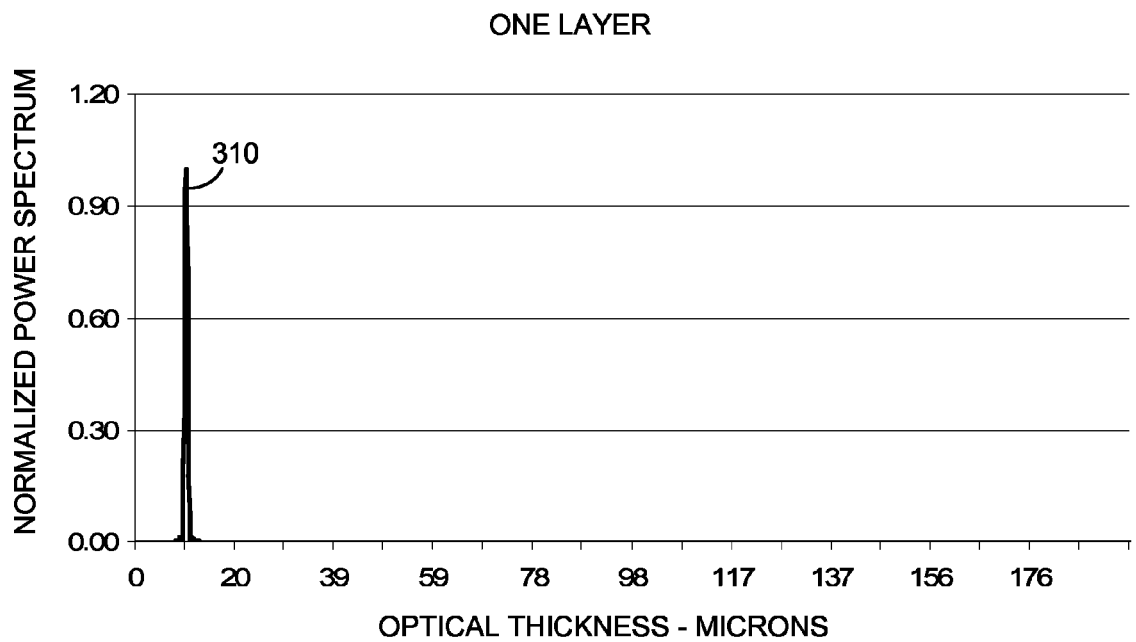
FIGS. 7A-7D illustrate a plot of the power spectrum after performing a bilinear transform and a Fourier transform of the reflectance data to the optical thickness domain for a sample structure of four layers, particularly illustrating the relation between the various relevant peaks.

FIG. 7A illustrates the transformed reflection amplitudes, as described above in relation to FIG. 5, in the optical thickness domain after growth of layer 4 directly on the substrate, where the x-axis represent optical thickness expressed in microns (μm) and the y-axis represents normalized power spectrum. Peak 310 is identified in FIG. 7A as having an optical thickness, $\theta_4$, of 10 μm, i.e. at an optical thickness appropriate for a refractive index of 5 and a thickness of 1 μm, and represents the interface between layer 4 and the substrate, i.e. the first interface and has a normalized value of 1.

Figure 7B:
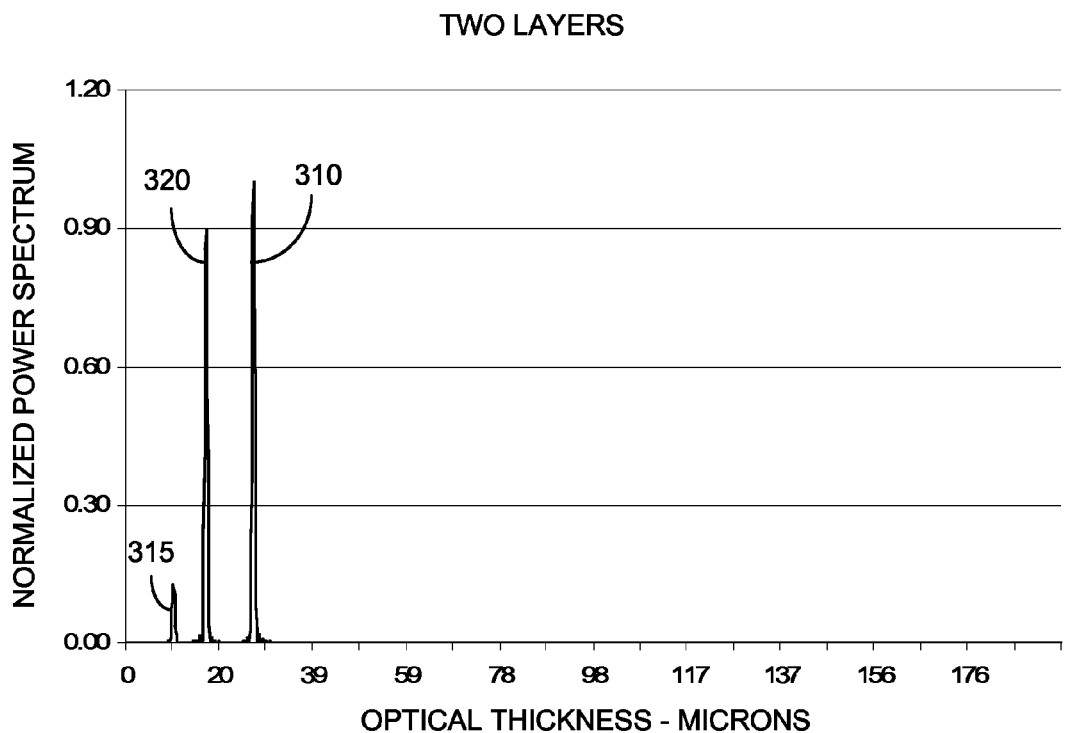

FIG. 7B illustrates the transformed reflection amplitudes, as described above in relation to FIG. 5, in the optical thickness domain after growth of layer 3 directly on the layer 4, where the x-axis represent optical thickness expressed in microns (μm) and the y-axis represents normalized power spectrum. Three peaks are illustrated. Peak 310 representing the interface between layer 4 and the substrate, i.e. the second interface, has been shifted by the additional optical thickness of layer 3, i.e. by $\theta_3$, since the light must pass through layer 3 to arrive at layer 4, and thus appears at an optical thickness of 26.8 μm. The amplitude of the peak has been changed by the optical impact of layer 3 and has a normalized value of 1. Peak 320 is associated with the transition between layer 3 and layer 4, i.e the first interface, and appears at an optical thickness of 16.8 μm and has a normalized value of 0.88. Peak 315 does not reflect an actual interface between single layers, and appears at the optical thickness of 10 μm, i.e. at the optical thickness of $\theta_4$ and has a normalized value of 0.12.

Figure 7C:
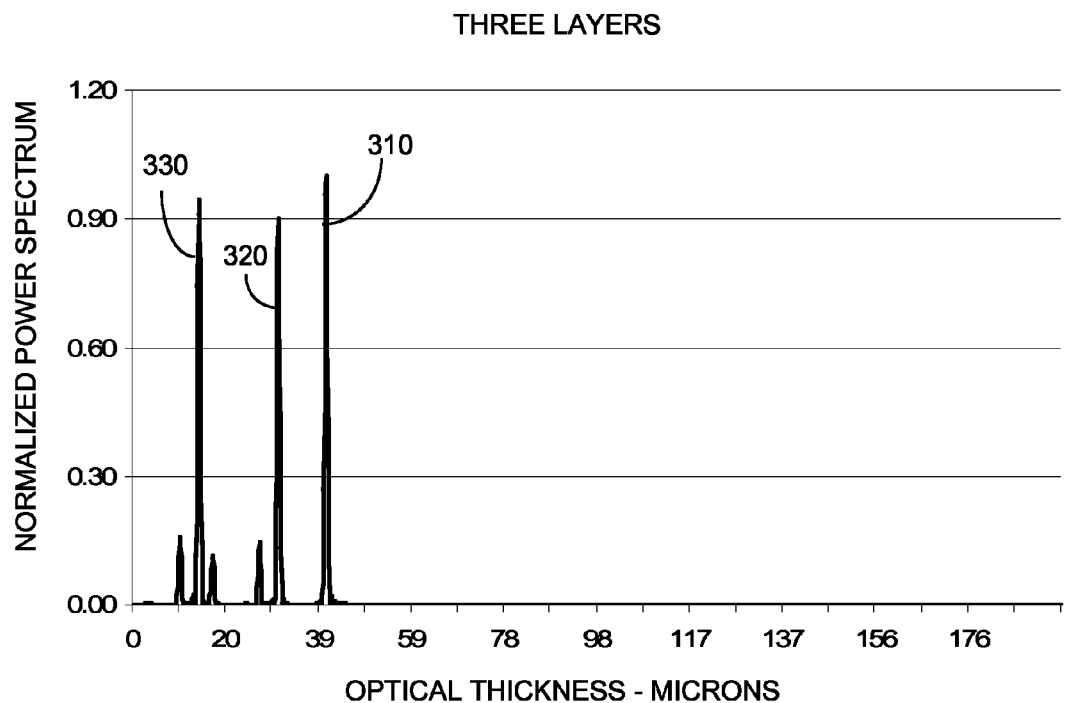

FIG. 7C illustrates the transformed reflection amplitudes, as described above in relation to FIG. 5, in the optical thickness domain after growth of layer 2 directly on the layer 3, where the x-axis represent optical thickness expressed in microns (μm) and the y-axis represents normalized power spectrum. Six peaks are observed. Peak 310 representing the interface between layer 4 and the substrate, i.e. the third interface, has been shifted from the optical thickness value of FIG. 7A by the additional optical thickness of layer 2 and 3, i.e. by $\theta_3+\theta_2$, since the light must pass through layers 2 and 3 to arrive at layer 4, and thus appears at an optical thickness of 40.8 μm and, as indicated above, has a normalized value of 1.0. Peak 320 is associated with the transition between layer 3 and layer 4, i.e. interface 2, and has been shifted from the optical thickness value of FIG. 7B by the additional optical thickness of layer 2, i.e. by $\theta_2$, since the light must pass through layer 2 to arrive at layer 3, and thus appears at an optical thickness of 30.8 μm and has a normalized value of 0.88. The amplitude of the peak has been changed by the optical impact of layer 2. Peak 330 is associated with the transition between layer 2 and layer 3, i.e. the first interface, and appears at an optical thickness of 14.0 μm and has a normalized value of 0.93. The balance of the peaks do not reflect an actual interface between single layers, and advantageously appear at the optical thickness of peaks found during the growth of previous layer, i.e. at the optical thickness of relevant peaks of FIGS. 7A-7B. The optical thickness between peaks 310 and 320 are unchanged between the two layer illustration of FIG. 7B and the three layer illustration of FIG. 7C.

Figure 7D:
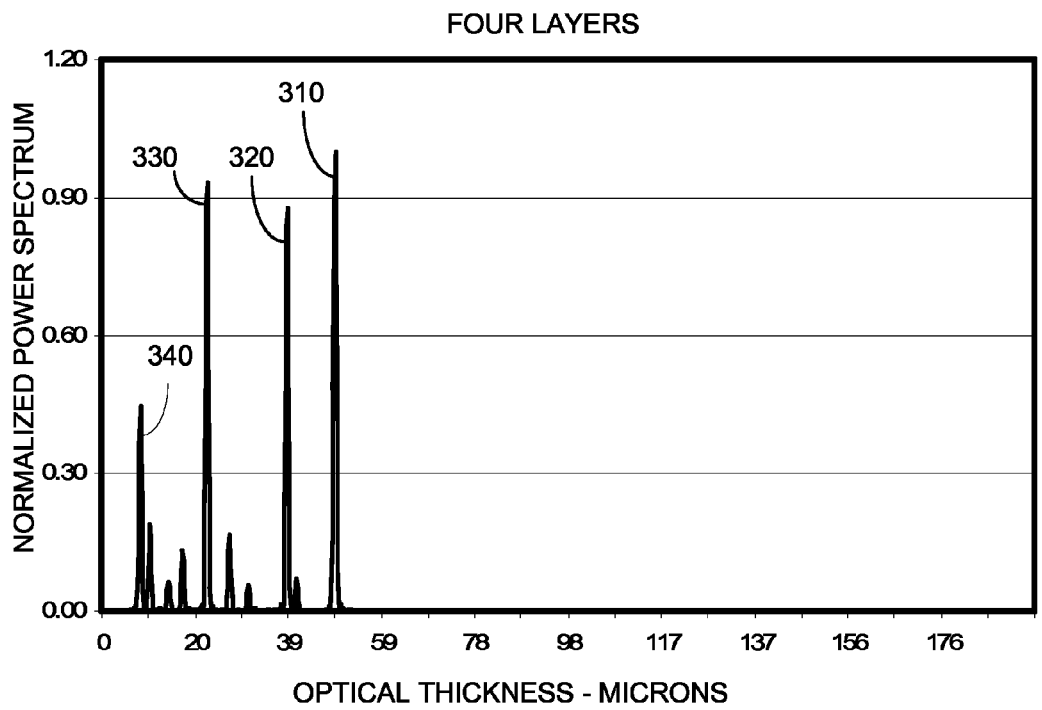

FIG. 7D illustrates the transformed reflection amplitudes, as described above in relation to FIG. 5, in the optical thickness domain after growth of layer 1 directly on the layer 2, where the x-axis represent optical thickness expressed in microns (μm) and the y-axis represents normalized power spectrum. Ten peaks are observed. Peak 310 representing the interface between layer 4 and the substrate, i.e. the fourth interface, has been shifted from the optical thickness value of FIG. 7A by the additional optical thickness of layers 1, 2 and 3, i.e. by $\theta_1+\theta_2+\theta_3$ since the light must pass through layers 1, 2 and 3 to arrive at layer 4, and thus appears at an optical thickness of 48.8 μm and is set to a normalized value of 1.0. Peak 320 is associated with the transition between layer 3 and layer 4, i.e. interface 3, and has been shifted from the optical thickness value of FIG. 7B by the additional optical thickness of layers 1 and 2, i.e. by $\theta_1+\theta_2$, since the light must pass through layers 1 and 2 to arrive at layer 3, and thus appears at an optical thickness of 38.8 μm and has a normalized value of 0.88. The amplitude of the peak has been changed by the optical impact of layers 1 and 2. Peak 330 is associated with the transition between layer 2 and layer 3, i.e. interface 2, and has been shifted by the additional optical thickness of layer 1, i.e. by $\theta_1$, since the light must pass through layer 1 to arrive at layer 2, and thus appears at an optical thickness of 22 μm and has a normalized value of 0.93. The amplitude of the peak has been changed by the optical impact of layer 1. Peak 340 is associated with the transition between layer 1 and layer 2, i.e. the first interface, and appears at an optical thickness of 8.0 μm and has a normalized value of 0.44. The balance of the peaks do not reflect an actual interface between single layers, and advantageously appear at the optical thickness of peaks found during the growth of previous layer, i.e. at the optical thickness of relevant peaks of FIGS. 7A-7C. The optical thickness between peaks 310 and 320 are unchanged between the two layer illustration of FIG. 7B, the three layer illustration of FIG. 7C and the four layer illustration of FIG. 7D. The optical thickness between peaks 320 and 330 are unchanged between the three layer illustration of FIG. 7C and the four layer illustration of FIG. 7D.

Figure 8:
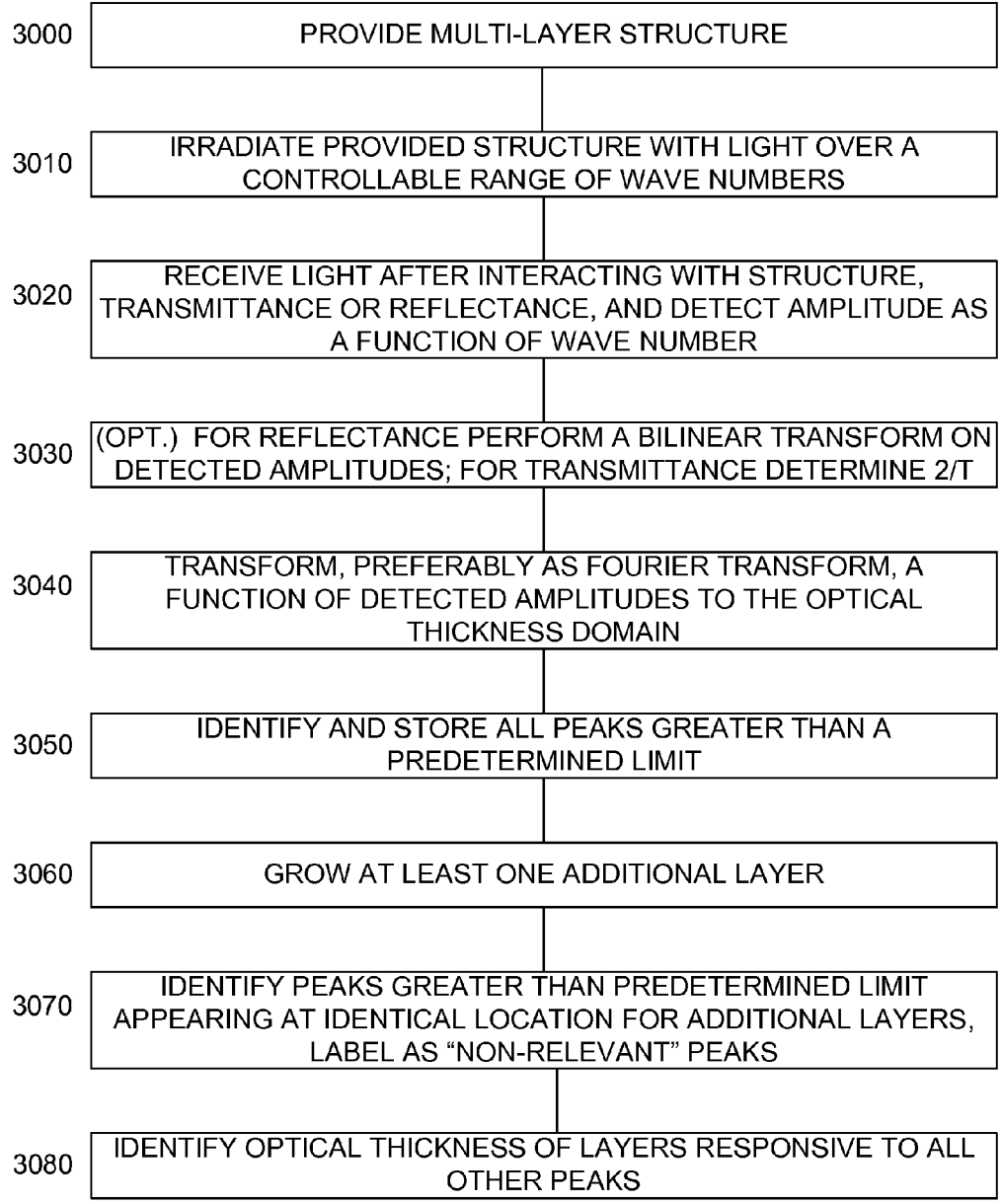
FIG. 8 illustrates a high level flow chart of the operation of the apparatus of either FIG. 1A or FIG. 2B to determine actual thickness of layers in a multi-layer structure.

FIG. 8 illustrates a high level flow chart of the operation of the apparatus of either FIG. 1A or FIG. 2B to determine actual thickness of layers in a multi-layer structure. In stage 3000 a multi-layer structure is provided, the thickness or refractive index of whose current layers are to be determined. In stages 3010-3040, the multi-layer structure of stage 3000 is analyzed optically as described above in relation to stages 1000-1030 of FIG. 5. In stage 3050 the optical thickness of all peaks greater than a predetermined minimum noise level are identified and stored.

In stage 3060 at least one additional layer is grown, and in stage 3070, after performing irradiation and transforming to the optical thickness domain, all peaks greater than the predetermined minimum noise level are identified and compared with the stored peaks of stage 3050. Any peaks appearing at a stored location are labeled as non-relevant peaks, as described above in relation to FIG. 7A-FIG. 7D. The balance of the peaks represent actual single interfaces. In one embodiment, in the event that the total number of actual peaks is greater than the maximal expected number of peaks previously calculated, the system outputs an error signal or visual indication advising that an extra parasitic layer, or layers, has been formed.

In stage 3080, the optical thickness of each of the layers of the provided structure of stage 3000 are identified responsive to peaks not labeled as "not relevant" in stage 3070. Preferably, stages 3060 and 3070 are performed for multiple layers to ensure consistency of stage 3080.

Figure 9:
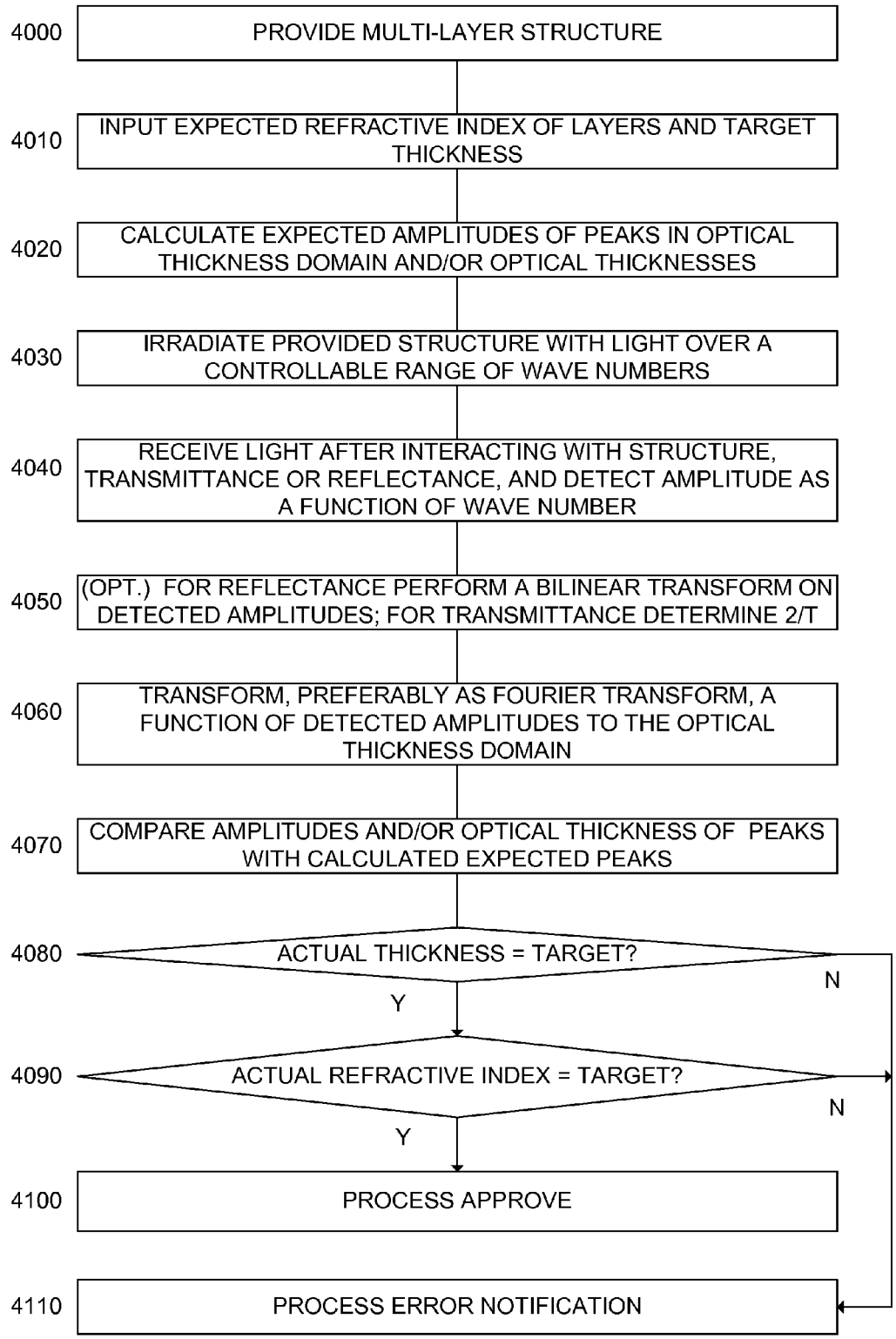
FIG. 9 illustrates a high level flow chart of the operation of the apparatus of either FIG. 1A or FIG. 2B to determine actual thickness of layers and/or refractive index in a multi-layer structure responsive to target parameters.

FIG. 9 illustrates a high level flow chart of the operation of the apparatus of either FIG. 1A or FIG. 2B to determine actual thickness of layers and/or refractive index of layers in a multi-layer structure, responsive to input target parameters. In stage 4000 a target multi-layer structure is provided, the thickness or refractive index of whose current layers are to be determined. In stage 4010 expected thicknesses and refractive indexes of layers of the multi-layer structure of stage 4000 are input. In stage 4020, expected amplitudes of peaks in the optical thickness domain and/or the optical thickness of the peaks are calculated, responsive to EQs. 5, 6, 8 and 9A.

In stages 4030-4060, the multi-layer structure of stage 4000 is analyzed optically as described above in relation to stages 1000-1030 of FIG. 5. In stage 4070 the peaks determined in stage 4060 are compared with the calculated expected peaks of stage 4020. In one embodiment, in the event that the total number of actual peaks is greater than the maximal expected number of peaks previously calculated, the system outputs an error signal or visual indication advising that an extra parasitic layer, or layers, has been formed.

In stage 4080, the actual thickness of the layers are compared with the target layer thickness, responsive to the amplitudes of the peaks. In particular, the amplitudes of the peaks enable calculation of the respective refractive indexes using EQs. 25-28, and thus based on the calculated values of n and the measured values of the optical thickness, the thickness of each layer can be calculated, as explained above. The refractive index measurement is preferably done one layer at a time. In the event that the actual thickness of the layers are not consonant within tolerance of the target thickness, in stage 4110 a process error notification signal is generated. Optionally, the process error notification signal provides full information regarding the difference between the target thickness and the measured thickness. In the event that the layer thickness has not achieved the target thickness, alternately a signal to continue layer production is output.

In the event that in stage 4080 the actual thickness of the layers is consonant within tolerance of the target thickness, in stage 4090 the refractive indexes of the multi-layer structure is compared with the target refractive index of stage 4010. In the event that the actual refractive index of the layers are not consonant within tolerance of the target refractive index, in stage 4110 a process error notification signal is generated. Optionally, the process error notification signal provides full information regarding the difference between the target refractive index and the measured refractive index. In the event that in stage 4090 the actual refractive index of the layers is consonant within tolerance of the target refractive index, in stage 4100 a signal indicative that the process is within tolerance is output.

During the optical layers growth process it might happen that interface and spurious peaks appear at close to, or even at, identical optical thicknesses. This co-existence of two peaks at about the same location causes an overlap effect. The overlap can create a resultant peak whose amplitude is higher than, or lower than, expected for the interface peak. In other words, the amplitudes of some interface peaks will therefore differ from the expected calculated values during such an overlap occurrence, without being indicative of a process error.

The overlap situation can be better understood by reference to the above described multi-layer optical material example. If we continue the growth process of layer 1 of FIG. 7D up to 1.6 μm, instead of stopping it at 1 μm, we will achieve the spectrum of FIG. 10, where the x-axis represent optical thickness expressed in microns (μm) and the y-axis represents normalized power spectrum. Because of overlap, we observe only 8 peaks instead of the expected 10 peaks. The interface peaks occur at the optical thicknesses of 12.8, 26.8, 43.6 and 53.6 μm. These are the same peaks labeled as 340, 330, 320 and 310, respectively at FIG. 7D, but shifted by 4.8 μm due to the additional 0.6 μm growth. The amplitude of peaks 320 and 310 are unchanged between FIG. 7D and FIG. 10; while the amplitude of peak 330 decreased significantly from 0.93 at FIG. 7D to 0.35 at FIG. 10 because of overlap with a spurious peak at $\theta_3+\theta_4$. Note that 0.93 is the expected analytical normalized value.

The overlap effect is preferably taken into account in one of a variety of techniques described herein, the particular technique depending on the method used for interface peaks identification. We have the following three possibilities to take into account.

First Overlap Embodiment

As explained above, interface peaks are recognizable during in-situ measurements by observing which peaks in the spectrum shift during the growth process. Spurious peaks remain at a fixed optical thickness location during the growth process, i.e. they are static, whereas actual peaks shift with the growth or deposition of each subsequent layer. Since interface peaks are recognized independently of their amplitude, thickness determination, which is dependent on the distance between identified peaks, is not affected by the overlap. However, the amplitude is relevant to the determination of refractive index, which is particularly relevant to inter-diffusion process problems, as described above in relation to FIGS. 5, 6, 8 and 9.

To alleviate this issue, in the event that the amplitude of an interface peak is not as anticipated by EQ. 8, in a preferred embodiment a calculation is performed, using EQ. 3, to determine if a spurious peak is expected to occur close to its same optical thickness position. In the event that such a spurious peak is found, we identify this situation as an overlap and disregard the peak amplitude value as an indicative for fabrication process failure. In the event that no such spurious peak is found responsive to EQ. 3, the peak amplitude value variance is indicative of a possible process error to report, as described above in relation to stages 2150 and 4110.

Second Overlap Embodiment

Interface peaks at the i-layer growth process are recognized by comparing spectra of present and previous layers analysis, as described above in relation to FIG. 6. Peaks occurring at the same optical thicknesses between subsequent layer analyses, i.e. peaks that are found to be at the same optical thickness between subsequent layer growth, or deposition, are labeled as potentially spurious. So, in the event that overlap occurs, we do not take into account all interface peaks, since we are disregarding those labeled as potentially spurious. Since we have a-priori knowledge of amplitudes and relative positions of interface peaks, i.e. information based on the planned composition of the target structure, as described above in relation to stage 1040, as well as information developed from the analysis of previous layers, the required information is derived for those interface peaks which are labeled as potentially spurious. In particular, optical thicknesses and/or refractive indexes related to peaks labeled potentially spurious are determined by using results from either the previous layer process or the expected values, or a combination thereof. Potentially spurious peaks which are then identified as relevant are then relabeled as "interface peaks affected by overlap", wherein amplitude information is not to be used as is, but must be derived from expected, or previously stored values.

For example let us assume we are growing the last layer, i.e. "layer-1". After comparing the normalized power spectrum of layer-1 vs. the normalized power spectrum of layer-2 and labeling spurious peaks, we identify that we have fewer peaks than interfaces. According to amplitudes and relative positions the peak at interface "i" is lacking. We know the optical thickness value $\theta 2+\theta 3+ \ldots +\theta i$ from analysis of previous layers, and we estimate $\theta 1$ based on the expected optical thickness distance from the leftmost interface peak at our current normalized power spectrum. We calculate $\theta 1+\theta 2+\theta 3+ \ldots +\theta i$, and then determine, at the current normalized power spectrum, what peak is found within a predetermined range around this optical thickness and identify it as the "i" interface peak, which is affected by overlap.

Figure 10:
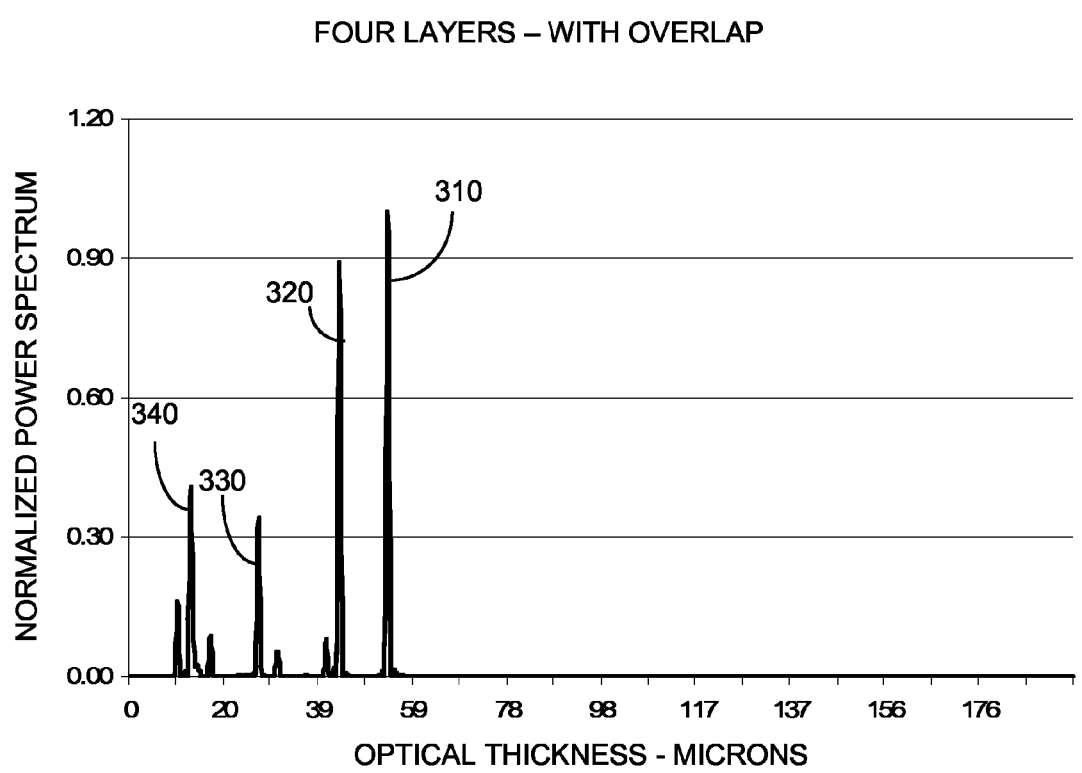
FIG. 10 illustrates a plot of the power spectrum after performing a bilinear transform and a Fourier transform of the reflectance data to the optical thickness domain for a sample structure of four layers exhibiting a peak overlap.

For our example of FIG. 10, we would initially disregard peak 330. After understanding that the peak at $\theta 1+\theta 2$ is lacking, we obtain from FIG. 7D $\theta 2=14$ μm and from FIG. 10 $\theta 1=12.8$ μm; so the interface peak should be located at about $\theta 1+\theta 2 \sim 26.8$ μm. Therefore, we identify the peak at 26.8 μm, i.e. peak 330, as an interface peak affected by overlap.

Third Overlap Embodiment

Identification of interface peaks is performed by means of their expected amplitude and relative position between themselves. No a-priori knowledge in regard to layer thicknesses is assumed. Once we do not succeed in identifying an interface peak "i" according to its amplitude, i.e. the peak amplitude is not consonant with the expected amplitude, we use information of spurious peaks related to such interface. We check from EQ. 3 what spurious peaks depend on "$\theta i$". We pick one of such spurious peaks whose amplitude in the normalized power spectrum matches the non-consonant peak, we use its optical thickness for calculations. For example, if we initially identified all peaks out of "i", according to EQ. 3 we have spurious peaks at $\theta i-1+\theta i$, $\theta i+\theta i+1$, $\theta i-2+\theta i-1+\theta i$. We can pick the peak $\theta i-1+\theta i$ responsive to its expected amplitude, we calculate $\theta i-1$ from its interface peak and we calculate $\theta i$.

The third overlap embodiment may be utilized with the second overlap embodiment. Each of the first and second overlap embodiments represent cases where layer parameters are determined during growth of multi-layer structures. The measurement of refractive index for the layer in deposition should preferably be performed at a layer thickness either less than or greater than the layer thickness exhibiting overlap.

If the amplitude of the first left interface peak, i.e. the interface peak associated with the lowest optical thickness in the normalized power spectrum, does not change with growth process, we understand that no overlap has taken place.

Assuming (for simplicity) that layer-1 is the last deposited layer, the condition for no overlap at the first interface peak is $n1 \cdot d1 \neq n2 \cdot d2 \neq \ldots nN \cdot dN$. Since the thicknesses of the deposited layers are measured during the processes, it is possible to calibrate the system to perform refractive index measurement at appropriate circumstances without overlap, i.e. the refractive index is to be determined at an optical thickness which does not result in overlap even if this requires determination of the refractive index prior to completion of growth or deposition of the layer.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to". The term "connected" is not limited to a direct connection, and connection via intermediary devices is specifically included.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. An apparatus arranged to analyze a multi-layer optical material structure, the apparatus comprising:
a control unit,
a light source arranged to irradiate a target structure; and a light receiver in communication with said control unit and arranged to receive said irradiated light from said light source after interaction with the target structure, said control unit comprising a processor and a memory, said memory storing machine readable instructions which cause said processor to:

receive a planned composition of the target multi-layer structure;

detect, in cooperation with said light receiver, an amplitude of the received light as a function of wavelength;

perform a transform of a function of said detected amplitudes to an optical thickness domain;

determine, responsive to the received planned composition of the target multi-layer structure, at least one of optical thickness and amplitude of expected peaks of said performed transform to the optical thickness domain which correspond with interactions with single interface between layers;

identify spurious peaks which do not correspond with interfaces between layers;

identify, responsive to said expected peaks, actual peaks of said performed transform to the optical thickness domain which correspond with interfaces between layers;

and determine at least one physical characteristic of the target structure responsive to said identified actual peaks while not utilizing said identified spurious peaks in said determining, wherein said function of said detected amplitudes is performed as $$B^{(N)} = B^0 \left( 1 + \sum_{k=1}^{N} \sum_{p=1}^{N-k+1} B_p^k \cos 4\pi \sum_{m=p}^{p+k-1} n_m d_m w \right),$$

where $$B_p^k = \frac{4 r_{p-1,p} \cdot r_{p+k-1,p+k}}{\prod_{q=p}^{p+k} (1 + r_{q-1,q}^2)},$$

$$B^0 = \prod_{q=1}^{N+1} \frac{1 + r_{q-1,q}^2}{1 - r_{q-1,q}^2},$$

$$r_{q-1,q} = \frac{n_{q-1} - n_q}{n_{q-1} + n_q}$$

and where, utilizing the received planned composition of the target multi-layer structure, $n_m$ is the refractive index of layer m, $n_q$ is the refractive index of layer q, $d_m$ is the thickness of layer m, w represents the wave number, the k-superscript indicates groups of k adjacent layers of the received planned composition, and the p subscript indicates the starting layer for each group.

2. The apparatus of claim 1, wherein said determined at least one physical characteristic is one of:
an actual thickness of at least one layer; and
an actual refractive index of at least one layer.

3. The apparatus of claim 1, wherein said control unit is arranged to perform said determination after growth or deposition of each of a plurality of layers, and wherein said machine readable instructions further cause said processor to:
confirm, after growth or deposition of at least one subsequent layer, that one of an actual thickness of previous layers and an actual refractive index of previous layers remains unchanged, and in an event that said one of the actual thickness of previous layers and the actual refractive index of previous layers has changed, output an error signal.

4. The apparatus of claim 1, wherein said control unit is arranged to perform said determination after growth or deposition of each of a plurality of layers, and wherein said machine readable instructions further cause said processor to:
identify changes in amplitude of said identified actual peaks corresponding to interfaces between previous layers, and output a process error indication responsive to said identified amplitude changes.

5. The apparatus of claim 1, wherein said determination of at least one physical characteristic of the target structure comprises:
calculate one of:
an actual thickness of each layer as it is added: and
a refractive index of each layer as it is added.

6. The apparatus of claim 1, wherein said determination of at least one physical characteristic of the target structure comprises:
calculate one of:
an actual thickness of each layer of a multi-layer structure; and
an actual refractive index of each layer of a multi-layer structure.

7. A method of analysis of a multi-layer structure, where the multi-layer optical material structure exhibits refractive index steps greater than 20%, the method comprising:
detecting an amplitude of a light as a function of wavelength after interaction with a target structure;
transforming a function of said detected amplitudes to an optical thickness domain;
determining, responsive to a planned composition of the target structure, at least one of optical thickness and amplitude of expected peaks of said performed transform to the optical thickness domain which correspond with interfaces between layers;
identifying, responsive to said expected peaks, actual peaks of said performed transform to the optical thickness domain which correspond with interfaces between layers; and
determining at least one physical characteristic of the target structure responsive to said identified actual peaks,
wherein said interaction is transmittance through the target multi-layer structure, and wherein said method further comprises computing twice a reciprocal of the amplitudes of the said received irradiated light as a function of wave number, and wherein said function of said detected amplitudes is said computed twice the reciprocal.

8. The method of claim 7, further comprising:
identifying spurious peaks which do not correspond with interfaces between layers,
wherein said determining at least one physical characteristic does not utilize said identified spurious peaks.

9. The method of claim 7, wherein said determined at least one physical characteristic is one of:
an actual thickness of at least one layer; and
an actual refractive index of at least one layer.

10. The method of claim 7, wherein said determining is performed after growth or deposition of each of a plurality of layers, and wherein the method further comprises:

confirming, after growth or deposition of at least one subsequent layer, that one of an actual thickness of previous layers remains unchanged and an actual refractive index of previous layers, and in an event that said one of the actual thickness of previous layers and the actual refractive index of previous layers has changed, outputting an error signal.

11. The method of claim 7, wherein said determining is performed after growth or deposition of each of a plurality of layers, and wherein the method further comprises:

identifying changes in amplitude of said identified actual peaks corresponding to interfaces between previous layers, and outputting a process error indication responsive to said identified amplitude changes.

12. The method of claim 10, wherein said determining at least one physical characteristic comprises:

calculating one of:
an actual thickness of each layer as it is added; and
an actual refractive index of each layer as it is added.

13. The method of claim 7, wherein said determining of at least one physical characteristic comprises:

calculating one of:
an actual thickness of each layer of a multi-layer structure; and
an actual refractive index of each layer of a multi-layer structure.

14. An apparatus arranged to analyze a multi-layer optical material structure having refractive index steps greater than 20% between layers, the apparatus comprising:

a control unit,
a light source arranged to irradiate a target structure; and
a light receiver in communication with said control unit and arranged to receive said irradiated light from said light source after interaction with the target structure,
said control unit comprising:
an amplitude detection functionality arranged to detect an amplitude of the received light as a function of wavelength;
a Fourier transform functionality arranged to perform a transform to an optical thickness domain of a function of said detected amplitudes;
a target determination functionality arranged to determine, responsive to a planned composition of the target semiconductor, at least one of optical thickness and amplitude of expected peaks of said performed transform to the optical thickness domain which correspond with interfaces between layers;
an identification functionality arranged to identify, responsive to said expected peaks, actual peaks of said performed transform to the optical thickness domain of said bilinear transformed amplitudes which correspond with interfaces between layers; and
a calculation functionality arranged to calculate an actual thickness of each layer responsive to said identified actual peaks,
wherein said function of said detected amplitudes is performed as $$B^{(N)} = B^0 \left( 1 + \sum_{k=1}^{N} \sum_{p=1}^{N-k+1} B_p^k \cos 4\pi \sum_{m=p}^{p+k-1} n_m d_m w \right),$$

where $$B_p^k = \frac{4 r_{p-1,p} \cdot r_{p+k-1,p+k}}{\prod_{q=p}^{p+k} (1 + r_{q-1,q}^2)},$$

$$B^0 = \prod_{q=1}^{N+1} \frac{1 + r_{q-1,q}^2}{1 - r_{q-1,q}^2},$$

$$r_{q-1,q} = \frac{n_{q-1} - n_q}{n_{q-1} + n_q}$$

and
where, utilizing the received planned composition of the target multi-layer structure, $n_m$ is the refractive index of layer m, $n_q$ is the refractive index of layer q, $d_m$ is the thickness of layer m, "w" represents the wave number, the k-superscript indicates groups of k adjacent layers of the received planned composition, the p subscript indicates the starting layer for each group.

* * * * *